US008192932B2

(12) United States Patent
Shuman et al.

(10) Patent No.: US 8,192,932 B2
(45) Date of Patent: *Jun. 5, 2012

(54) COVALENT JOINING OF DNA STRANDS TO RNA STRANDS CATALYZED BY VACCINIA TOPOISOMERASE

(75) Inventors: Stewart Shuman, New York, NY (US);
JoAnn Sekiguchi, Belmont, MA (US);
John Comiskey, Carlsbad, CA (US);
Joseph Fernandez, Carlsbad, CA (US);
James Hoeffler, Carlsbad, CA (US);
Robert Marcil, Carlsbad, CA (US)

(73) Assignees: Sloan-Kettering Institute For Cancer Research, New York, NY (US);
Invitrogen Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/658,764

(22) Filed: Feb. 12, 2010

(65) Prior Publication Data
US 2010/0317064 A1    Dec. 16, 2010

Related U.S. Application Data

(63) Continuation of application No. 10/666,486, filed on Sep. 19, 2003, now Pat. No. 7,662,556, which is a continuation of application No. 09/096,927, filed on Jun. 12, 1998, now Pat. No. 6,653,106.

(60) Provisional application No. 60/046,405, filed on Jun. 12, 1997.

(51) Int. Cl.
*C12Q 1/68* (2006.01)
*C12P 21/06* (2006.01)
*C12P 19/34* (2006.01)
*C07H 21/02* (2006.01)

(52) U.S. Cl. ...... 435/6.1; 435/69.1; 435/91.1; 435/91.2; 435/91.3; 435/91.5; 435/91.51; 435/183; 536/23.1

(58) Field of Classification Search .................. 435/6.1, 435/69.1, 91.1–91.51, 183; 536/23.1
See application file for complete search history.

(56) References Cited

U.S. PATENT DOCUMENTS

| 4,661,450 A | 4/1987 | Kempe et al. |
| 4,800,159 A | 1/1989 | Mullis et al. |
| 5,624,826 A | 4/1997 | Kato et al. |
| 5,746,997 A | 5/1998 | Reed |
| 5,766,891 A | 6/1998 | Shuman et al. |
| 6,238,884 B1 | 5/2001 | Short et al. |
| 6,280,977 B1 | 8/2001 | Liang et al. |
| 6,291,213 B1 | 9/2001 | Rothstein et al. |
| 6,548,277 B1 | 4/2003 | Shuman et al. |
| 6,653,106 B1 | 11/2003 | Shuman et al. |
| 7,662,556 B2 | 2/2010 | Shuman et al. |

FOREIGN PATENT DOCUMENTS

| EP | 0 373 914 B1 | 7/1994 |
| EP | 0 625 572 B1 | 4/2001 |
| WO | WO 85/04898 | 11/1985 |
| WO | WO 94/29443 | 12/1994 |
| WO | WO 96/19497 A1 | 6/1996 |
| WO | WO 96/34981 | 11/1996 |
| WO | WO 97/24455 | 7/1997 |
| WO | WO 98/20122 | 5/1998 |
| WO | WO 98/55502 | 12/1998 |
| WO | WO 98/56943 | 12/1998 |
| WO | WO 00/12687 | 3/2000 |
| WO | WO 00/56878 | 9/2000 |
| WO | WO 01/62892 | 8/2001 |
| WO | WO 01/62943 | 8/2001 |
| WO | WO 02/16594 | 2/2002 |

OTHER PUBLICATIONS

Shuman et al, Site specific interaction of vaccinia virus topoisomerase with base and sugar moieties in duplex DNA, 1993, The journal of biological chemistry, 268, 18943-18950.*
Shuman-1, Novel approach to molecular cloning and polynucleotide synthesis using vaccinia DNA topoisomerase, 1994, The journal of biological chemistry, 269, 32678-32684.*
Maruyama et al, Oligocapping: a simple method to replace the cap structure of eukaryotic mRNAs with oligoribonucleotides, 1994, Gene, 138, 171-174.*
Arnott et al., "DNA-RNA Hybrid Secondary Structures", J. Mol. Biol., Apr. 20, 1986, 188(4), 631-640.
Carninci et al., "High Efficiency Selection of Full-Length cDNA by Improved Biotinylated cap Trapper", DAN Research, Feb. 28, 1997, 4, 61-66.
Carninci et al., "High-Efficiency Full-length cDNA Cloning by Biotinylated CAP Trapper", Genomics, Nov. 1, 1996, 37(3), 327-336.
Chenchick et al., "Full Length cDNA Cloning and Determination of mRNA 5' and 3' Ends by Amplification of Adaptor Ligated cDNA", Biotechniques, Sep. 1996, 21(3), 526-534.
Cheng and Shuman, "A catalytic domain of eukaryotic DNA topoisomerase I", J. Biol. Chem., May 8, 1998, 273(19), 115898-115895.
Cheng and Shuman, "DNA strand transfer catalyzed by vaccinia topoisomerase: ligation of DNAs containing a 3' mononucleotide overhang", Nucleic Acids Res., May 1, 2000, 28(9), 1893-1898.
Cheng and Shuman, "Recombinogenic flap ligation pathway for intrinsic repair of topoisomerase IB-induced double-strand breaks", Mol. Cell. Biol., Nov. 2000, 20(21), 8059-8068.
Cheng and Shuman, "Site-specific DNA transesterification by vaccinia topoisomerase: Role of specific phosphates and nucleosides", Biochemistry, Dec. 14, 1999, 38(50), 16599-16612.
Cheng et al., "Conservation of structure and mechanism between eukaryotic topoisomerase I and site-specific recombinases", Cell , May 20, 1998, 92(6), 841-850.

(Continued)

Primary Examiner — Stephen Kapushoc
Assistant Examiner — Narayan Bhat
(74) Attorney, Agent, or Firm — Woodcock Washburn, LLP

(57) ABSTRACT

The present invention provides a method of covalently joining a DNA strand to an RNA strand, a method of tagging a 5' end of an RNA molecule, a DNA-RNA molecule which has been joined in vitro by the use of a topoisomerase, a method of tagging a 5' end of an mRNA, and a method of isolating and cloning full-length gene sequences using capped mRNA after subtraction of non-capped RNA.

19 Claims, 13 Drawing Sheets

OTHER PUBLICATIONS

Cheng et al., "Mutational analysis of 39 residues of vaccinia DNA topoisomerase identifies Lys-220, Arg-223, and Asn-228 as important for covalent catalysis", J. Biol. Chem., Sep. 15, 1997, 272(13), 8263-8269.

Chong et al., "Single-column purification of free recombinant proteins using a self-cleavable affinity tag derived from a protein splicing element", Gene, Jun. 19, 1997, 192(2), 271-281.

DiGate and Marians, "Molecular cloning and DNA sequence analysis of Escherichia coli topoB, the gene encoding topoisomerase III", J. Biol. Chem., Oct. 25, 1989, 264(30), 17924-17930.

Edery et al., "An efficient strategy to isolate full-length cDNAs based on an mRNA cap retention procedure (CAPture)", Mol. Cell. Biol., Jun. 1995, 15(6), 3363-3371.

Ericsson et al., "Characterization of ts16, a temperature-sensitive mutant of vaccinia virus", J. Virol., Nov. 1995, 69(11), 7072-7086.

Gross and Shuman, "Vaccinia virions lacking the RNA helicase nucleoside triphosphate phosphohydrolase II are defective in early transcription", J. Virol., Dec. 1996, 70(12), 8549-8555.

Haghighat and Sonenberg, "eIF4G dramatically enhances the binding of eIF4E to the mRNA 5'-cap structure", J. Biol. Chem., Aug. 29, 1997, 272(35), 21677-21680.

Haghighat et al., "The eIF4G-eIF4E complex is the target for direct cleavage by the rhinovirus 2A proteinase", J. Virol., Dec. 1996, 70, 8444-8450.

Henningfeld and Hecht, "A model for topoisomerase I-mediated insertions and deletions with duplex DNA substrates containing branches, nicks, and gaps", Biochemistry, May 9, 1995, 34(18), 6120-6129.

Invitrogen Corporation, Carlsbad, California, Catalog, 1998, pp. 18, 29, 43, 44, 49-52.

Janknecht et al., "Rapid and efficient purification of native histidine-tagged protein expressed by recombinant vaccinia virus", Proc. Natl. Acad. Sci., Oct. 15, 1991, 88, 8972-8976.

Kane and Shuman, "Vaccinia virus morphogenesis is blocked by a temperature-sensitive mutation in the I7 gene that encodes a virion component", J. Virol., May 1993, 67(5), 2689-2698.

Kato et al., "Construction of a human full-length cDNA bank", Gene, Dec. 15, 1994, 150, 243-250.

Klemm et al., "Peptide inhibitors of DNA cleavage by tyrosine recombinases and topoisomerases", J. Mol. Biol., Jun. 23, 2000, 299(5), 1203-1216.

Klemperer et al., "Identification and characterization of the orf virus type 1 topoisomerase", Virology, Jan. 10, 1995, 206, 203-215.

Krogh and Shuman, "Catalytic mechanism of DNA topoisomerase IB", Mol. Cell, Jun. 2000, 5(6), 1035-1041.

Krogh and Shuman, "DNA strand transfer catalyzed by vaccinia topoisomerase: peroxidolysis and hydroxylaminolysis of the covalent protein-DNA intermediate", Biochemistry, Mary 30, 2000, 39(21), 6422-6432.

Krogh and Shuman, "Vaccinia topoisomerase mutants illuminate conformational changes during closure of the protein clamp and assembly of a functional active site", J. Biol. Chem., Jul. 5, 2001, 276, 36091-36099.

Krogh et al., "Effect of 2'-5' phosphodiesters on DNA transesterification by vaccinia topoisomerase", J. Biol. Chem., Apr. 3, 2001, 276(24), 20907-20912.

Krogh et al., "Melanoplus sanguinipes entomopoxvirus DNA topoisomerase: site-specific DNA transesterification and effects of 5'-bridging phosphorothiolates", Virology, Nov. 25, 1999, 264(2), 441-451.

Liu et al., "Mapping the 5' and 3' ends of tetrahymena thermophila mRNAs using ligase mediated amplification of cDNA ends (RLM-RACE)", Nucleic Acids Res., Oct. 25, 1993, 21(21), 4954-4960.

Lockard et al., "Labeling of Eukaryotic Messenger RNA 5' Terminus with Phosporus-32: se of Tobacco Acid Pyrophosphatase for Removal of Cap Structures", Gene Amplification and Analysis, Apr. 10, 1989, 2, 229-251.

Maruyama et al., "Oligo-Capping: A simple method to replace the cap structure of eukaryotic mRNAs with oligonucleotides", Gene, Jan. 28, 1994, 138, 171-174.

Matthews et al., "Analytical strategies for the use of DNA probes", Anal. Biochem., Feb. 15, 1998, 169, 1-25.

Morham and Shuman, "Phenotypic selection and characterization of mutant alleles of a eukaryotic DNA topoisomerase I", Genes. Dev., Apr. 1990, 4(4), 515-524.

Morham et al., Covalent and Noncovalent DNA Binding by Mutants of Vaccinia DNA Topoisomerase I, Journal of Biological Chemistry, Aug. 5, 1992, 267(22), 15984-15992.

Palaniyar et al., "SFV topoisomerase: sequence specificity in a genetically mapped interval", Virology, Jul. 15, 1996, 221, 351-354.

Petersen and Shuman, "DNA strand transfer reactions catalyzed by vaccinia topoisomerase: hydrolysis and glycerololysis of the covalent protein-DNA intermediate", Nucleic Acids Res., Jun. 1, 1997, 25(11), 2091-2097.

Petersen and Shuman, "Histidine 265 is important for covalent catalysis by vaccinia topoisomerase and is conserved in all eukaryotic type I enzymes", J. Biol. Chem., Feb. 14, 1997, 272(7), 3891-3896.

Petersen et al., "Characterization of a DNA topoisomerase encoded by Amsacta moore entomopoxvirus", Virology, Apr. 14, 1997, 230(2), 197-206.

Petersen et al., "Mutations within a conserved region of vaccinia topoisomerase affect the DNA cleavage-religation equilibrium", J. Mol. Biol., Oct. 25, 1996, 1263(2), 181-195.

Salazar et al., "The DNA strand in DNA:RNA hybrid duplexes is neither B-form nor A-form in solution", Biochemistry, Apr. 27, 1993, 32(16), 4207-4215.

Schaefer, "Revolutions in Rapid Amplification of cDNA Ends. New Strategies for Polymerase Chain Reaction Cloning of Full Length cDNA Ends", Ananlytical Biochemistry, May 20, 1995, 227, 255-273.

Schmitt et al., "Affinity purification of histidine-tagged proteins", Mol. Biol. Reports, Oct. 1993, 18(3), 223-230.

Sekiguchi and Shuman, "Covalent DNA binding by vaccinia topoisomerase results in unpairing of the thymine base 5' of the scissile bond", J. Biol. Chem., Aug. 9, 1996, 271(32), 19436-1942.

Sekiguchi and Shuman, "Domain structure of vaccinia DNA ligase", Nucleic Acids Res., Feb. 15, 1997, 25(4), 727-734.

Sekiguchi and Shuman, "Identification of contacts between topoisomerase I and its target DNA by site-specific photocrosslinking", EMBO J., Jun. 1, 1996, 15(13), 3448-3457.

Sekiguchi and Shuman, "Mutational analysis of vaccinia virus topoisomerase identifies residues involved in DNA binding", Nucleic Acids Res., Sep. 15, 1997, 25(18), 3649-3656.

Sekiguchi and Shuman, "Nick sensing by vaccinia virus DNA ligase requires a 5' phosphate at the nick and occupancy of the adenylate binding site on the enzyme", J. Virol., Dec. 1997, 71(12), 9679-9684.

Sekiguchi and Shuman, "Proteolytic footprinting of vaccinia topoisomerase bound to DNA", J. Biol. Chem., May 12, 1995, 270(19), 11636-11645.

Sekiguchi and Shuman, "Requirements for noncovalent binding of vaccinia topoisomerase I to duplex DNA", Nucleic Acids Res., Nov. 3, 1994, 22(24), 5360-5365.

Sekiguchi and Shuman, "Site-specific ribonuclease activity of eukaryotic DNA topoisomerase I", Mol. Cell, Dec. 1997, 1(1), 89-97.

Sekiguchi and Shuman, "Stimulation of vaccinia topoisomerase I by nucleoside triphosphates", J. Biol. Chem., Nov. 25, 1994, 269(47), 29760-29764.

Sekiguchi and Shuman, "Vaccinia topoisomerase binds circumferentially to DNA", J. Biol. Chem., Dec. 16, 1994, 269(50), 31731-31734.

Sekiguchi et al., "Kinetic anlysis of DNA and RNA strand transfer reactions catalyzed by vaccinia topoisomerase", J. Biol. Chem., Jun. 20, 1997, 272(25), 15721-15728.

Sekiguchi et al., "Mechanism of inhibition of vaccinia DNA topoisomerase by novobiocin and coumermycin", J. Biol. Chem., Jan. 26, 1996, 271(4), 2313-2322.

Sekiguchi et al., "Resolution of a Holliday junction by vaccinia topoisomerase requires a spacer DNA segment 3' of the CCCTT/ cleavage sites", Nucleic Acids Res., Jul. 15, 2000, 28(14), 2658-2663.

Sekiguchi et al., "Resolution of Holliday junctions by eukaryotic DNA topoisomerase I", Proc. Natl. Acad. Sci., Jan. 23, 1996, 93(2), 785-789.

Shatkin, "Capping of eukaryotic mRNAs", Cell, Dec. 1976, 9(4), 645-653.

Shuman and Moss, "Identification of a vaccinia virus gene encoding a type I DNA topoisomerase", Proc. Natl. Acad. Sci., Nov. 1, 1987, 84, 7478-7482.

Shuman and Prescott, "Specific DNA cleavage and binding of vaccinia virus DNA topoisomerase I", J. Biol. Chem., Oct. 15, 1990, 265, 17826-17836.

Shuman and Turner, "Site-specific interaction of vaccinia virus topoisomerase I with base and sugar moieties in duplex DNA", J. Biol. Chem., Sep. 5, 1993, 268(25), 18943-18950.

Shuman et al., "Characterization of vaccinia virus DNA topoisomerase I expressed in *Escherichia coli*", J. Biol. Chem., Nov. 5, 1988, 263, 16401-16407.

Shuman et al., "Insertional mutagenesis of the vaccinia virus gene encoding a type I DNA topoisomerase: evidence that the gene is essential for virus growth", Virology, May 1989, 170(1), 302-306.

Shuman et al., "Intramolecular synapsis of duplex DNA by vaccinia topoisomerase", EMBO J., Nov. 3, 1997, 16(21), 6584-6589.

Shuman et al., "Mapping the active-site tyrosine of vaccinia virus DNA topoisomerase I", Proc. Natl. Acad. Sci., Dec. 1, 1989, 86(24), 9793-9797.

Shuman, "Analysis of topoisomerase-DNA interactions by electrophoretic mobility shift assay", Methods Mol. Biol., Oct. 20, 2001, 95, 65-74.

Shuman, "DNA strand transfer reactions catalyzed by vaccinia topoisomerase I", J. Biol. Chem., Apr. 1992, 267, 8620-8627.

Shuman, "Novel Approaches to Molecular Cloning and Polynucleotide Synthesis Using Vaccinia DNA Topoisomerase", J. Biol. Chem., Dec. 23, 1994, 269, 32678-32684.

Shuman, "Polynucleotide ligase activity of eukaryotic topoisomerase I", Mol. Cell., Sep. 15, 1998, 1(5), 741-748.

Shuman, "Recombination mediated by vaccinia virus DNA topoisomerase I in *Escherichia coli* is sequence specific", Proc. Natl. Acad. Sci., Nov. 15, 1991, 88(22), 10104-10108.

Shuman, "Site-specific DNA cleavage by vaccinia virus DNA topoisomerase I. Role of nucleotide sequence and DNA secondary structure", J. Biol. Chem., Jan. 25, 1991, 266(3), 1796-1803.

Shuman, "Site-specific interaction of vaccinia virus topoisomerase I with duplex DNA. Minimal DNA substrate for strand cleavage in vitro", J. Biol. Chem., Jan. 15, 1991, 266(17), 11372-11379.

Shuman, "Two classes of DNA end-joining reactions catalyzed by vaccinia topoisomerase I", J. Biol. Chem., Aug. 25, 1992, 267, 16755-16758.

Shuman, "Vaccinia DNA topoisomerase I promotes illegitimate recombination in *Escherichia coli*", Proc. Natl. Acad. Sci., May 1989, 86(10), 3489-3493.

Shuman, "Vaccinia virus DNA ligase: specificity, fidelity, and inhibition", Biochemistry, Dec. 12, 1995, 34, 16138-16147.

Shuman, "Vaccinia virus DNA topoisomerase: a model eukaryotic type IB enzyme", Biochim. Biophys. Acta., Oct. 1, 1998, 1400(1-3), 321-337.

Stivers et al., "Stereochemical outcome and kinetic effects of Rp- and Sp-phosphorothioate substitutions at the cleavage site of vaccinia type I DNA topoisomerase", Biochemistry, May 9, 2000, 39(18), 5561-5572.

Stivers et al., "Vaccinia DNA topoisomerase I: single-turnover and steady-state kinetic analysis of the DNA strand cleavage and ligation reactions", Biochemistry, Jan. 11, 1994, 33(1), 327-339.

Theus, "A simple assay for determining the capping efficiencies of RNA polymerases used for in vitro transcription", Biotechniques, Nov. 1990, 9(5), 610-615.

Wang and Shuman, "Deletions at the carboxyl terminus of vaccinia DNA topoisomerase affect DNA binding and enhance distributivity in DNA relaxation", Biochemistry, Apr. 1, 1997, 36(13), 3909-3916.

Wang et al., "Mutational analysis of 26 residues of vaccinia DNA topoisomerase identifies Ser-204 as important for DNA binding and cleavage", Biochemistry, Jul. 1, 1997, 36(26), 7944-7950.

Wexler et al., "A procedure to amplify cDNA from dsRNA templates using the Polymerase chain reaction", Methods Mol. Cell. Biol., 1991, 2, 273-279.

Wittschieben and Shuman, "Mechanism of DNA transesterification by vaccinia topoisomerase: catalytic contributions of essential residues Arg-130, Gly-132, Tyr-136 and Lys-167", Nucleic Acids Res., Jun. 1997, 25(15), 3001-3008.

Wittschieben and Shuman, "Mutational analysis of vaccinia DNA topoisomerase defines amino acid residues essential for covalent catalysis", J. Biol. Chem., Nov. 25, 1994, 269(47), 29978-29983.

Wittschieben et al., "Replacement of the active site tyrosine of vaccinia DNA topoisomerase by glutamate, cysteine or histidine converts the enzyme into a site-specific endonuclease", Nucleic Acids Res., Jan. 15, 1998, 26(2), 490-496.

Woodfield et al., "Vaccinia topoisomerase and Cre recombinase catalyze direct ligation of activated DNA substrates containing a 3'-paranitrophenyl phosphate ester", Nucleic Acids Res., Sep. 1, 2000, 28(17), 3323-3331.

Yang et al., "A eukaryotic enzyme that can disjoin dead-end covalent complexes between DNA and type I topoisomerases", Proc. Natl. Acad. Sci., Oct. 15, 1996, 93(21), 11534-11539.

* cited by examiner

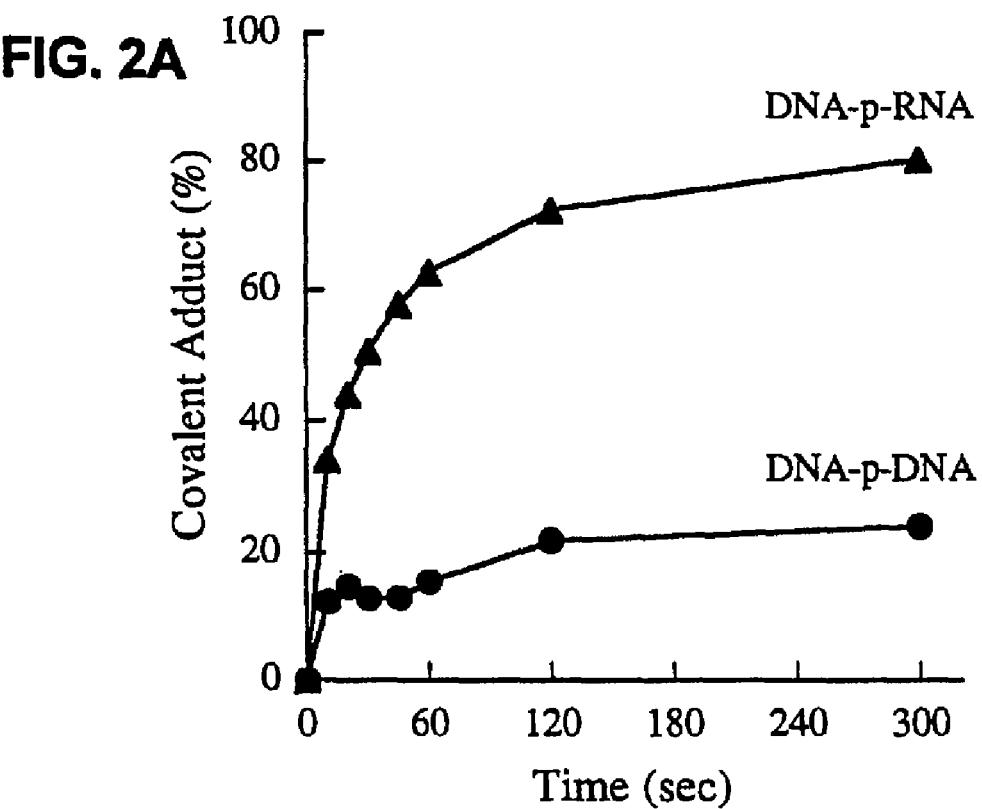
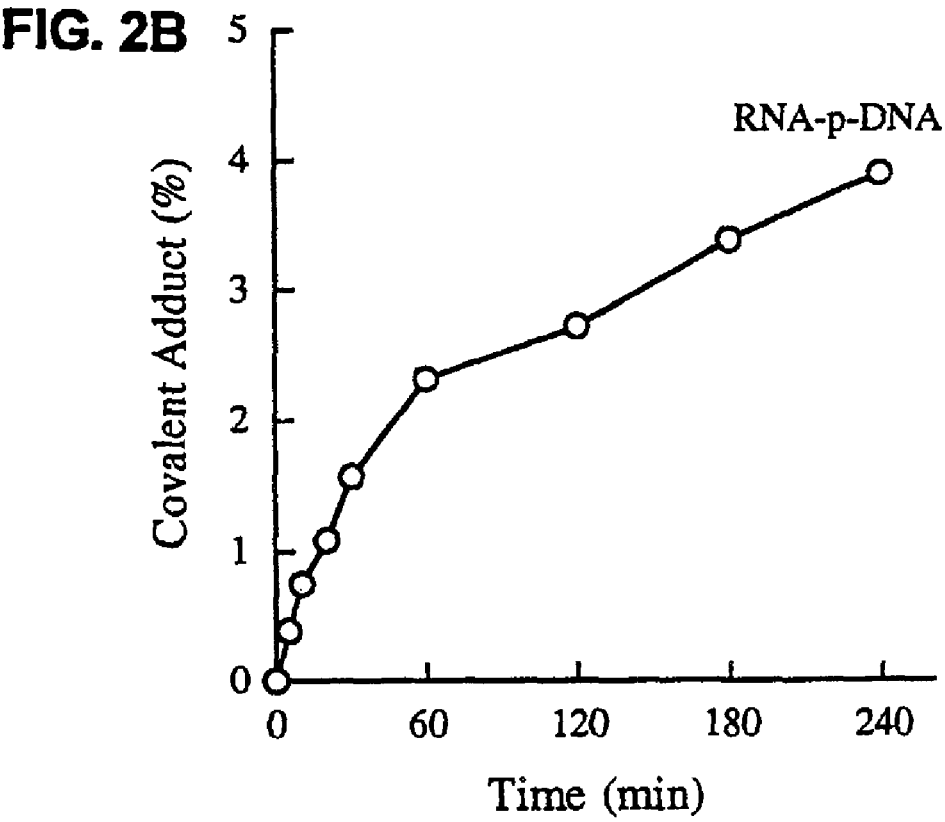

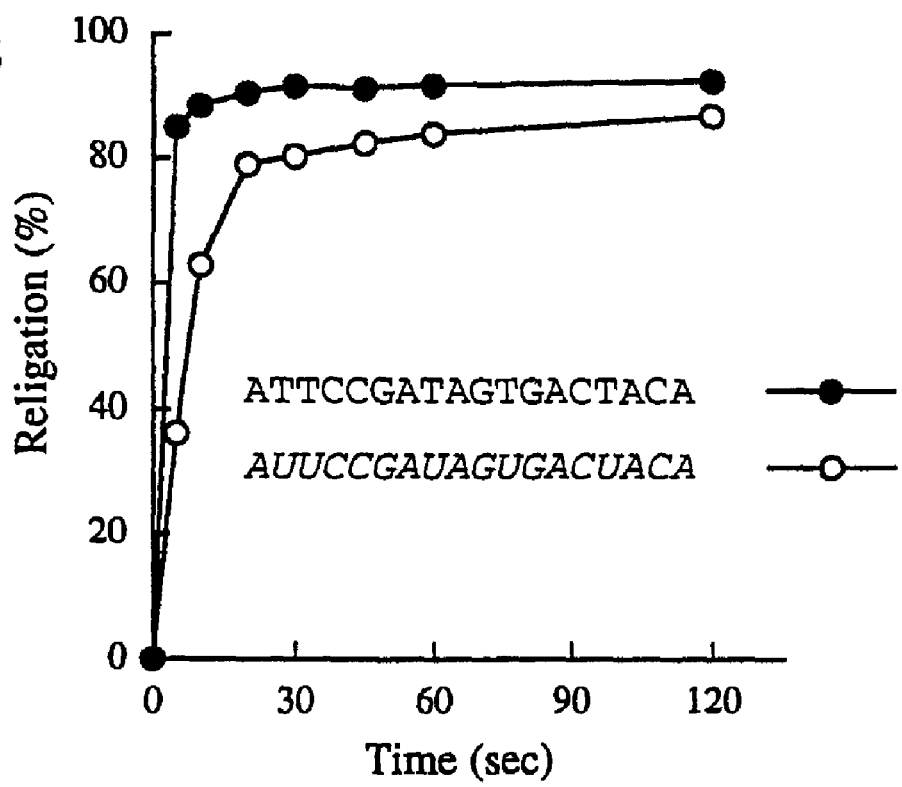

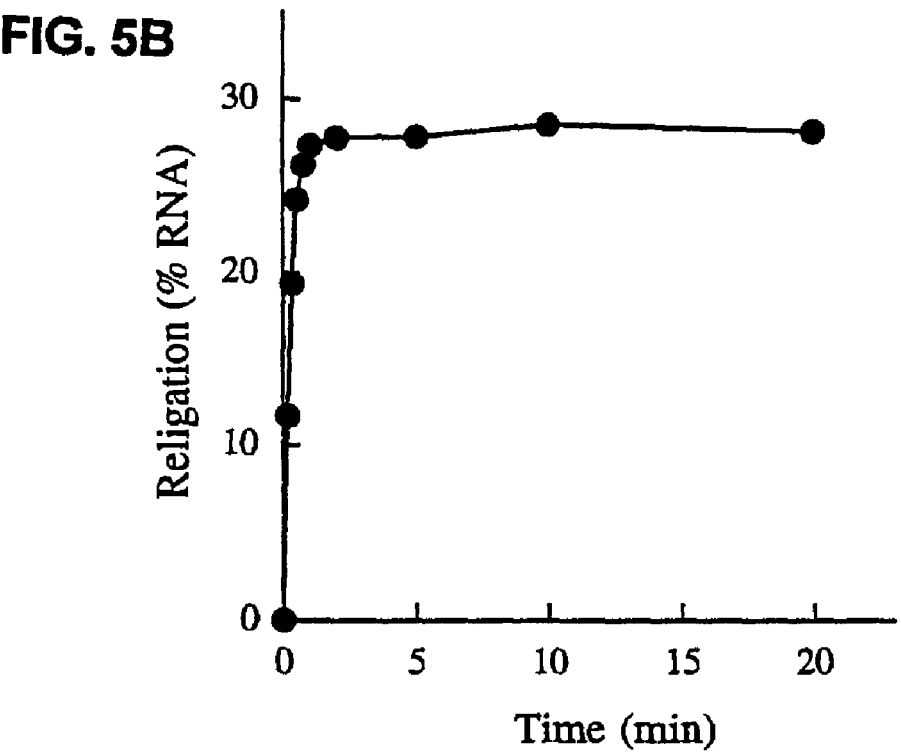

FIG. 6A
```
                    (Topo)
CGTGTCGCCCTT
GCACAGCGGGAATAAGGCTATCACTGATGT
```
FIG. 6B
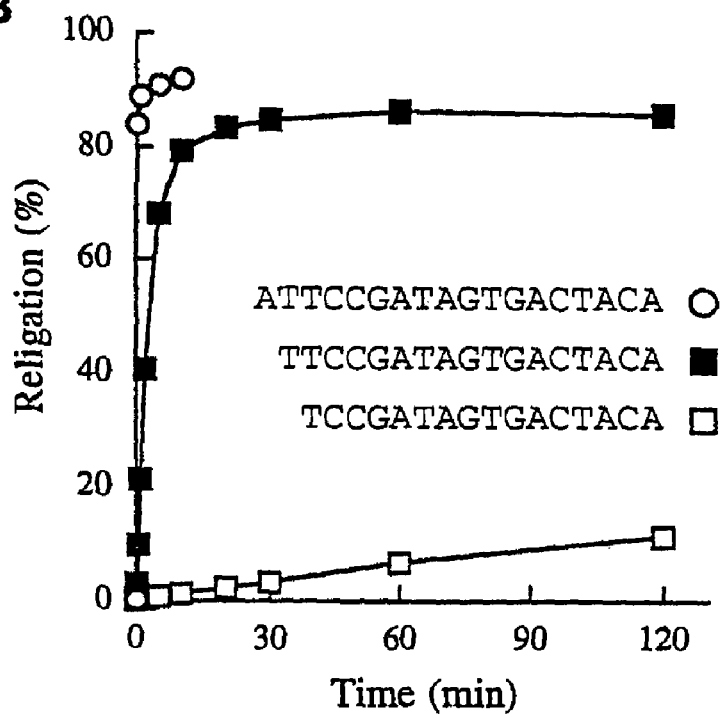
ATTCCGATAGTGACTACA ○
TTCCGATAGTGACTACA ■
TCCGATAGTGACTACA □
FIG. 6C
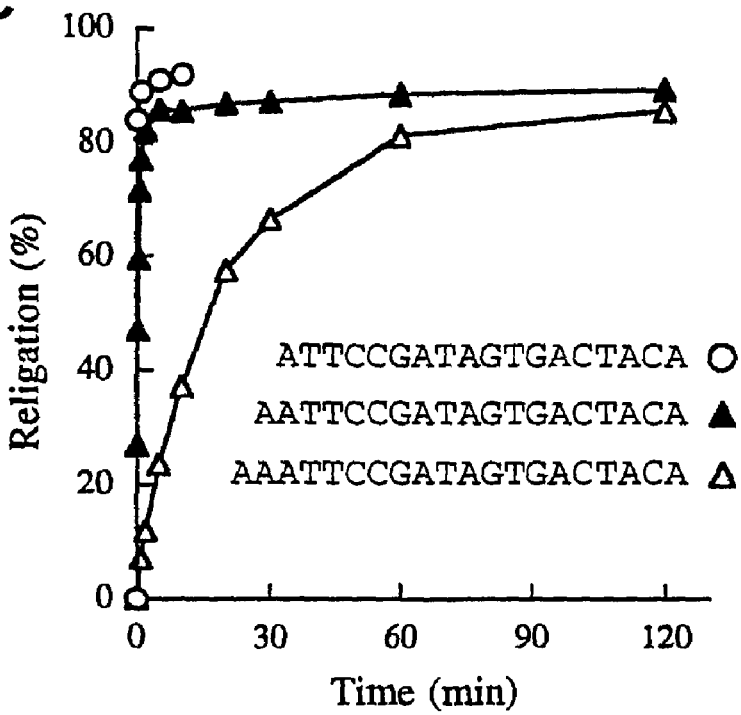
ATTCCGATAGTGACTACA ○
AATTCCGATAGTGACTACA ▲
AAATTCCGATAGTGACTACA △

— 50-mer product

— T7 transcript

PCR Product

Mini Prep Results

US 8,192,932 B2

COVALENT JOINING OF DNA STRANDS TO RNA STRANDS CATALYZED BY VACCINIA TOPOISOMERASE

This application is a continuation of U.S. Ser. No. 10/666,486, filed Sep. 19, 2003, now U.S. Pat. No. 7,662,556, issued Feb. 16, 2010, which is a continuation of U.S. Ser. No. 09/096,927, filed Jun. 12, 1998, now U.S. Pat. No. 6,653,106, issued Nov. 25, 2003, which claims the benefit of U.S. Provisional Application Ser. No. 60/046,405, filed Jun. 12, 1997, the contents of each of which are hereby incorporated by reference.

This invention was made with support under Grant No. GM46330 from the National Institutes of Health, U.S. Department of Health and Human Services. Accordingly, the United States Government has certain rights in the invention.

Throughout this application, various references are referred to within parentheses. Disclosures of these publications in their entireties are hereby incorporated by reference into this application to more fully describe the state of the art to which this invention pertains. Full bibliographic citations for these references may be found at the end of this application, preceding the sequence listing and claims.

BACKGROUND OF THE INVENTION

Vaccinia topoisomerase binds duplex DNA and forms a covalent DNA-(3'-phosphotyrosyl)-protein adduct at the sequence 5'-CCCTT'. The enzyme reacts readily with a 36-mer CCCTT strand (DNA-p-RNA) composed of DNA 5' and RNA 3' of the scissile bond. However, a 36-mer composed of RNA 5' and DNA 3' of the scissile phosphate (RNA-p-DNA) is a poor substrate for covalent adduct formation. Vaccinia topoisomerase efficiently transfers covalently held CCCTT-containing DNA to 5'-OH terminated RNA acceptors; the topoisomerase can therefore be used to tag the 5' end of RNA in vitro.

Religation of the covalently bound CCCTT-containing DNA strand to a 5'-OH terminated DNA acceptor is efficient and rapid ($k_{rel}$>0.5 sec$^{-1}$), provided that the acceptor DNA is capable of base-pairing to the noncleaved DNA strand of the topoisomerase-DNA donor complex. The rate of strand transfer to DNA is not detectably affected by base mismatches at the 5' nucleotide of the acceptor strand. Nucleotide deletions and insertions at the 5' end of the acceptor slow the rate of religation; the observed hierarchy of reaction rates is: +1 insertion >−1 deletion >+2 insertion >>−2 deletion. These findings underscore the importance of a properly positioned 5' OH terminus in transesterification reaction chemistry, but also raise the possibility that topoisomerase may generate mutations by sealing DNA molecules with mispaired or unpaired ends.

Vaccinia topoisomerase, a 314-amino acid eukaryotic type I enzyme, binds and cleaves duplex DNA at a specific target sequence 5'-(T/C)CCTT' (1-3). Cleavage is a transesterification reaction in which the Tp'N phosphodiester is attacked by Tyr-274 of the enzyme, resulting in the formation of a DNA-(3'-phosphotyrosyl) protein adduct (4). The covalently bound topoisomerase catalyzes a variety of DNA strand transfer reactions. It can religate the CCCTT-containing strand across the same bond originally cleaved (as occurs during the relaxation of supercoiled DNA) or it can ligate the strand to a heterologous acceptor DNA 5' end, thereby creating a recombinant molecule (5-7).

Duplex DNA substrates containing a single CCCTT target site have been used to dissect the cleavage and strand transfer steps. A cleavage-religation equilibrium is established when topoisomerase transesterifies to DNA ligands containing 18-bp of duplex DNA 3' of the cleavage site (8-11). The reaction is in equilibrium because the 5'-OH terminated distal segment of the scissile strand remains poised near the active site by virtue of the fact that it is stably base-paired with the nonscissile strand. About 20% of the CCCTT-containing strand is covalently bound at equilibrium (11). "Suicide" cleavage occurs when the CCCTT-containing substrate contains no more than fifteen base pairs 3' of the scissile bond, because the short leaving strand dissociates from the protein-DNA complex. In enzyme excess, >90% of the suicide substrate is cleaved (11).

The suicide intermediate can transfer the incised CCCTT strand to a DNA acceptor. Intramolecular strand transfer occurs when the 5'-OH end of the noncleaved strand of the suicide intermediate attacks the 3' phosphotyrosyl bond and expels Tyr-274 as the leaving group. This results in formation of a hairpin DNA loop (5). Intermolecular religation occurs when the suicide intermediate is provided with an exogenous 5'-OH terminated acceptor strand, the sequence of which is complementary to the single strand tail of the noncleaved strand in the immediate vicinity of the scissile phosphate (5). In the absence of an acceptor strand, the topoisomerase can transfer the CCCTT strand to water, releasing a 3'-phosphate-terminated hydrolysis product, or to glycerol, releasing a 3'-phosphoglycerol derivative (12). Although the hydrolysis and glycerololysis reactions are much slower than religation to a DNA acceptor strand, the extent of strand transfer to non-DNA nucleophiles can be as high as 15-40%.

The specificity of vaccinia topoisomerase in DNA cleavage and its versatility in strand transfer have inspired topoisomerase-based strategies for polynucleotide synthesis in which DNA oligonucleotides containing CCCTT cleavage sites serve as activated linkers for the joining of other DNA molecules with compatible termini (13). The present study examines the ability of the vaccinia topoisomerase to cleave and rejoin RNA-containing polynucleotides. It was shown previously that the enzyme did not bind covalently to CCCTT-containing molecules in which either the scissile strand or the complementary strand was composed entirely of RNA (9). To further explore the pentose sugar specificity of the enzyme, we have prepared synthetic CCCTT-containing substrates in which the scissile strand is composed of DNA- and RNA-containing halves. In this way, we show that the enzyme is indifferent to RNA downstream of the scissile phosphate, but is does not form the covalent complex when the region 5' of the scissile phosphate is in RNA form. Also assessed is the contribution of base-pairing by the 5' end of the acceptor strand to the rate of the DNA strand transfer reaction.

SUMMARY OF THE INVENTION

The present invention provides a method of covalently joining a DNA strand to an RNA strand comprising (a) forming a topoisomerase-DNA intermediate by incubating a DNA cleavage substrate comprising a topoisomerase cleavage site with a topoisomerase specific for that site, wherein the topoisomerase-DNA intermediate has one or more 5' single-strand tails; and (b) adding to the topoisomerase-DNA intermediate an acceptor RNA strand complementary to the 5' single-strand tail under conditions permitting a ligation of the 5' single-strand tail of the topoisomerase-DNA intermediate to the RNA acceptor strand and dissociation of the topoisomerase, thereby covalently joining the DNA strand to the RNA strand. The DNA cleavage substrate may be created by hybridizing a DNA strand having a topoisomerase cleavage site to one or more complementary DNA strands, thereby forming a DNA cleavage substrate having a topoisomerase cleavage site and a oligonucleotide leaving group located 3' of a scissile bond or may be a plasmid vector comprising a topoisomerase cleavage site.

The present invention also provides a covalent topoisomerase-DNA intermediate having a 5' single-strand tail.

Another aspect of the present invention provides a DNA-RNA molecule covalently joined by topoisomerase catalysis.

The present invention provides a covalently joined DNA-RNA molecule having a labeled 5' end.

The present invention further provides a method of tagging a 5' end of an RNA molecule comprising: (a) forming a topoisomerase-DNA intermediate by incubating a DNA cleavage substrate comprising a topoisomerase cleavage site with a topoisomerase specific for that site, wherein the topoisomerase-DNA intermediate has one or more 5' single-strand tails; and (b) adding to the topoisomerase-DNA intermediate a 5'-hydroxyl terminated RNA molecule complementary to the 5' single-strand tail under conditions permitting a ligation of the covalently bound DNA strand of the topoisomerase-DNA intermediate to the RNA molecule and dissociation of the topoisomerase, thereby forming a 5' end tagged DNA-RNA ligation product. The DNA cleavage substrate can be created, for example, by hybridizing a DNA strand having a topoisomerase cleavage site to a complementary DNA strand, thereby forming a DNA cleavage substrate having a topoisomerase cleavage site and a oligonucleotide leaving group located 3' of a scissile bond.

Another aspect of the present invention provides a 5' end tagged RNA molecule.

In another aspect the present invention also provides a DNA-RNA molecule which has been joined in vitro by the use of a topoisomerase.

The present invention further provides a method of tagging a 5' end of a capped messenger RNA comprising: a) isolating mRNA from cells or a tissue; b) removing an RNA cap structure from the isolated mRNA, resulting in a de-capped RNA; c) dephosphorylating the de-capped RNA, thereby forming a de-capped and dephosphorylated RNA; d) constructing a DNA cleavage substrate for topoisomerase having a topoisomerase cleavage site and a complementary strand, the complementary strand having a mixed or random base composition downstream of the topoisomerase cleavage site, the DNA cleavage substrate being designated as a DNA-(N) substrate; e) cleaving the DNA-(N) substrate with a topoisomerase, thereby forming a covalent topoisomerase-DNA-(N)M complex containing a 5' tail of mixed or random base composition on a noncleaved strand; and f) incubating the cleaved covalent topoisomerase-DNA-(N)M complex with the de-capped and dephosphorylated RNA formed in step (c) to form a 5' DNA-tagged DNA-RNA ligation product.

As used herein the number of bases (N) of the DNA cleavage substrate, designated supra as a DNA-(N) substrate, may be from one to four bases long.

The present invention also provides a method of isolating and cloning a capped mRNA after subtraction of non-capped RNA comprising: a) isolating mRNA from cells or a tissue; b) dephosphorylating the mRNA; c) incubating a cleaved topoisomerase-BioDNA-(N) complex with the dephosphorylated mRNA to form a 5' BioDNA-tagged DNA-RNA ligation product; d) removing the 5' BioDNA-tagged DNA-RNA ligation product and any unreacted cleaved topoisomerase-BioDNA-(N) complex by adsorption to streptavidin and recovering any nonadsorbed material, said material being enriched for RNA having a capped 5' end and being resistant to dephosphorylation in step (b), thereby being unable to react with the cleaved topoisomerase-BioDNA-(N) complex; e) removing of the 5' end cap from the enriched RNA recovered from the nonadsorbed material in step (d); f) dephosphorylating the de-capped RNA, thereby forming a de-capped and dephosphorylated RNA; g) incubating a cleaved topoisomerase-BioDNA-(N) complex with the de-capped and dephosphorylated RNA to form a 5' BioDNA-tagged DNA-RNA ligation product; h) affinity purifying the 5' DNA-tagged DNA-RNA ligation product; and i) PCR amplification of the decapped and dephosphorylated RNA of the DNA-RNA ligation product using a sense primer corresponding to a scissile strand of the topoisomerase cleavage substrate 5' of the site of cleavage and an antisense primer, said antisense primer being complementary to either a 3' poly(A) tail or to an internal RNA sequence.

The present invention also provides a method of obtaining full-length gene sequences comprising attaching a DNA tag to an isolated mRNA sequence and using the DNA-tagged mRNA as a template for DNA synthesis. DNA may be further inserted into an expression vector and used to express recombinant protein.

BRIEF DESCRIPTION OF THE FIGURES

FIG. 2A-B. Kinetics of cleavage of RNA-containing 36-mer substrates. Reaction mixtures contained (per 20 µl) 50 mM Tris-HCl (pH 8.0), 0.2 pmol of radiolabeled 36-mer substrate and 1 pmol of topoisomerase. Covalent adduct formation (% of input label transferred to the topoisomerase) is plotted as a function of the time of incubation at 37° C. (A) Cleavage of DNA-p-DNA and DNA-p-RNA; x-axis in sec. (B) Cleavage of RNA-p-DNA; x-axis in min.

FIGS. 3A-B. (SEQ ID NOS: 6-9) Strand transfer to an RNA acceptor. (A) The structures of the covalent topoisomerase-DNA complex (suicide intermediate) and the 18-mer acceptor strands (DNA or RNA) are shown. (B) Religation reactions were performed under single-turnover conditions as described under Materials and Methods. The extent of religation (expressed as the percent of input labeled DNA converted to the 30-mer strand transfer product) is plotted as a function of incubation time.

FIGS. 5A-B. (SEQ ID NOS: 6, 10, and 11) 5'DNA-tagging of RNA transcribed by T3 RNA polymerase. (A) The structures of the covalent topoisomerase-DNA donor complex and the RNA acceptor are shown. The 5'single-strand tail of the suicide intermediate is complementary to the 18 nucleotides at the 5'end of the T3 transcript. Reaction mixtures contained (per 15 ul) 50 mM Tris-HCl (pH 8.0), 0.3 M NaCl, and 0.1 pmol of $^{32}$P-GMP-labeled T3 transcript. (B) Religation was initiated by the addition of pre-formed topoisomerase-DNA donor (at a 10-fold molar excess over RNA acceptor). Incubation was at 37° C. Aliquots (15 µl) were removed at the times indicated and quenched immediately by adding SDS and EDTA. The samples were adjusted to 50% formamide, heated for 5 min at 95° C., and electrophoresed through a 12% polyacrylamide gel containing 7 M urea in TBE. Transfer of the 12-nucleotide DNA donor strand to the 5' end of the labeled 36-mer T3 transcript yielded a labeled 48-mer product. Conversion of input 36-mer to 48-mer was quantitated by scanning the gel with a phosphorimager.

FIGS. 6A-C. Kinetics of topoisomerase-catalyzed strand transfer reactions resulting in DNA deletions and insertions. (A) (SEQ ID NOS: 6 and 7) The structure of the pre-formed donor complex is shown at the top of the Figure. Religation reactions were performed under single-turnover conditions as described under Materials and Methods. All DNA acceptors were included at a 50-fold molar excess over the input CCCTT-containing substrate. (B) (SEQ ID NOS: 4, 12 and 13) Deletion formation. The structures of the completely base-paired 18-mer acceptor DNA oligonucleotide (open circle), a 17-mer oligonucleotide that anneals to the donor complex to leave a 1-nucleotide gap (filled square) and a 16-mer strand that anneals to leave a 2-nucleotide gap (square) are shown. (C) (SEQ ID NOS: 4, 14 and 15) Insertion formation. The structures of the completely base-paired 18-mer acceptor (open circle), a 19-mer oligonucleotide containing 1 extra 5'nucleotide (filled triangle) and a 20-mer acceptor containing 2 extra 5'nucleotides (triangle) are shown. The extent of religation is plotted as a function of incubation time.

FIG. 10A-B. Affinity Tagging of RNA Using Vaccinia Topoisomerase. (A) (SEQ ID NOS: 23, 24, 25, 24, 26, 27, and 24, respectively) The strand transfer reaction pathway is diagramed in the Figure. The biotinylated DNA substrate which contains a single topoisomerase recognition site is immobilized on the Dynabeads (Dynal) streptavidin solid support. The biotin moiety (indicated by the black square) is introduced at the 5'end of the CCCTT-containing strand via standard protocols for automated oligonucleotide synthesis. The purified vaccinia topoisomerase is reacted with the bead-bound DNA to form a covalent enzyme-DNA donor complex, as illustrated. Enzyme not bound to DNA is removed by washing the beads with buffer. The strand transfer reaction is initiated by addition of the [$^{32}$P]-CMP labeled T7 transcript which is dephosphorylated by prior treatment with alkaline phosphatase. The 5'single-strand tail of the donor complex is complementary to the 12 nucleotides at the 5'end of the T7 transcript. Religation of the covalently held biotinylated DNA strand to the T7 transcript is observed as conversion of the 30-mer RNA to a product of 50 nucleotides. The mixture was incubated at 37° C. for 15 min. The beads were then recovered by centrifugation, washed, and resuspended in 20 ul of buffer containing 0.8% SDS and 80% formamide. The samples were heated at 95° C. for 5 min, centrifuged for 5 min, then the supernatants were electrophoresed through a 12% polyacrylamide gel containing 7M urea in TEE buffer. (B) An autoradiograph of the gel is shown in the Figure. Lane B (Bound)-product of the strand transfer reaction bound to the Dynabeads; lane F (Free)-supernatant from the strand transfer reaction. The positions of the input 30-mer T7 transcript and the 50-mer product are shown at the right.

DETAILED DESCRIPTION OF THE INVENTION

Figure 1A:
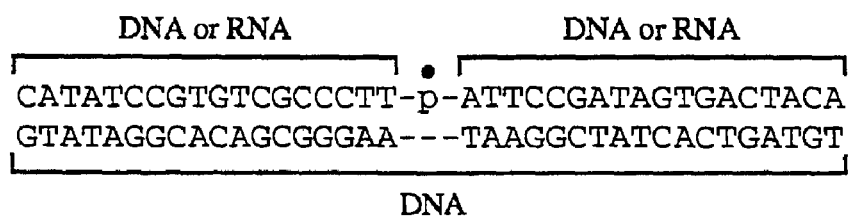
FIGS. 1A-B. Topoisomerase cleavage of DNA-p-RNA and RNA-p-DNA strands. (A) The 36-bp substrate used in the cleavage reactions is shown, with the $^{32}$P-labeled scissile phosphate indicated by the filled circle. The segments of the top strand (SEQ ID NOS: 3 and 4) flanking the scissile phosphate, which are either DNA or RNA, are bracketed; the bottom strand (SEQ ID NO: 5) is all-DNA. (B) Reaction mixtures (20 µl) containing 50 mM Tris-HCl (pH 8.0), 0.2 pmol of substrate (either DNA-p-RNA or RNA-p-DNA) and topoisomerase as indicated were incubated at 37° C. for 10 min. Covalent adduct formation (% of input label transferred to the topoisomerase) is plotted as a function of the amount of enzyme added.

Throughout this application, the following standard abbreviations are used to indicate specific nucleotides: C=cytosine A=adenosine U=uracil T=thymidine G=guanosine The present invention provides a method of covalently joining a DNA strand to an RNA strand comprising (a) forming a topoisomerase-DNA intermediate by incubating a DNA cleavage substrate comprising a topoisomerase cleavage site with a topoisomerase specific for that site, wherein the topoisomerase-DNA intermediate has one or more 5' single-strand tails; and (b) adding to the topoisomerase-DNA intermediate an acceptor RNA strand complementary to the 5' single-strand tail under conditions permitting a ligation of the covalently bound DNA strand of the topoisomerase-DNA intermediate to the RNA acceptor strand and dissociation of the topoisomerase, thereby covalently joining the DNA strand to the RNA strand. The DNA cleavage substrate may be created by hybridizing a DNA strand having a topoisomerase cleavage site to one or more complementary DNA strands, thereby forming a DNA cleavage substrate having a topoisomerase cleavage site and a oligonucleotide leaving group located 3' of a scissile bond or may be a plasmid vector comprising a topoisomerase cleavage site.

In an embodiment of the above-described method, the topoisomerase cleavage site is a sequence comprising CCCTT. In a preferred embodiment the topoisomerase is a vaccinia topoisomerase enzyme. In a further embodiment the vaccinia topoisomerase enzyme is a modified vaccinia topoisomerase enzyme. In another embodiment the DNA strand having a topoisomerase cleavage site is radiolabelled. In a preferred embodiment the radiolabel is $^{32}$P or a radiohalogen. Means for radio labeling nucleotides are well known in the art (see Ausubel, et. al., Short Protocols in Molecular Biology, 3rd ed., Wiley, 1995; U.S. Pat. No. 5,746,997 issued May 5, 1998). In another preferred embodiment the DNA strand having a topoisomerase cleavage site is labeled with a biotin moiety or another affinity purification tag such as chitin binding domain, glutathione-S-transferase, and the like. Methods of adding affinity labels to nucleotides are well known in the art (see Carniaci, et. al., Genomics 37: 327-336, 1996; Ausubel, et. al., supra). In an embodiment the topoisomerase-bound DNA intermediate and the acceptor RNA strand are ligated in vitro.

The present invention provides a covalent topoisomerase-DNA intermediate molecule having a 5' single-strand tail. In an embodiment of the covalent topoisomerase-DNA intermediate molecule, the 5' single-strand tail comprises a specific sequence. In another embodiment the covalent topoisomerase-DNA intermediate molecule having a 5' single-strand tail is generated by the above-described method of covalently joining a DNA strand to an RNA strand. In a further embodiment of the covalent topoisomerase-DNA intermediate molecule having 5' single-strand tail generated by the above-described method of the 5' single-strand tail comprises a specific sequence. In another embodiment of the covalent topoisomerase-DNA intermediate molecule having a 5' single-strand tail generated by step (a) of the above-described method the DNA strand is radiolabelled. In a preferred embodiment of the covalent topoisomerase-DNA intermediate molecule the radiolabel is $^{32}$P or a radiohalogen. In another embodiment of the covalent topoisomerase-DNA intermediate molecule having a 5' single-strand tail generated by step (a) of the above-described method, the DNA strand is affinity labeled. In a preferred embodiment of the covalent topoisomerase-DNA intermediate molecule, wherein the affinity label is a biotin moiety, a chitin binding domain, a glutathione-S-transferase moiety, and the like.

The present invention further provides a DNA-RNA molecule covalently joined by topoisomerase catalysis.

The present invention provides a DNA-RNA molecule covalently joined by the above-described method of covalently joining a DNA strand to an RNA strand. In a preferred embodiment the covalently joined DNA-RNA molecule has a 5' end label. In a further embodiment the 5' end label is $^{32}$P or a radiohalogen. In another embodiment the 5' end label is a biotin moiety, a chitin binding domain, a glutathione-S-transferase moiety, and the like.

The present invention provides a covalently joined DNA-RNA molecule having a labeled 5' end. In a preferred embodiment of the covalently joined DNA-RNA molecule the 5' end label is $^{32}$P or a radiohalogen. In another preferred embodiment of the covalently joined DNA-RNA molecule the 5' end label is a biotin moiety, a chitin binding domain, a glutathione-S-transferase moiety, and the like.

The present invention further provides a method of tagging a 5' end of an RNA molecule comprising: (a) forming a topoisomerase-DNA intermediate by incubating a DNA cleavage substrate comprising a topoisomerase cleavage site with a topoisomerase specific for that site, wherein the topoisomerase-DNA intermediate has one or more 5' single-strand tails; and (b) adding to the topoisomerase-DNA intermediate a 5'-hydroxyl terminated RNA molecule complementary to the 5' single-strand tail under conditions permitting a ligation of the 5' single-strand tail of the topoisomerase-DNA intermediate to the RNA molecule and dissociation of the topoisomerase, thereby forming a 5' end tagged DNA-RNA ligation product. The DNA cleavage substrate can be created, for example, by hybridizing a DNA strand having a topoisomerase cleavage site to a complementary DNA strand, thereby forming a DNA cleavage substrate having a topoisomerase cleavage site and a oligonucleotide leaving group located 3' of a scissile bond.

The RNA molecule can be the product of in vitro synthesis or can have been isolated from cells or tissues. Methods of synthesizing RNA in vitro are well known in the art (see, for example, Ausubel, et al, supra). Methods of isolating RNA from cells and/or tissues are also well known in the art (see, Ausubel, et al, supra). Cells and tissues suitable for use in obtaining RNA useful in the practice of the present invention include both animal cells and plant cells. Particularly preferred cells include mammalian cells (such as rodent cells, primate cells, and the like) and insect cells. RNA may also be isolated from prokaryotic cells such as bacteria.

In a preferred embodiment of the above-described method, the RNA molecule is a dephosphorylated after synthesis or isolation. In another preferred embodiment the dephosphorylation is achieved by treatment of the RNA molecule with alkaline phosphatase. In a preferred embodiment the topoisomerase is a vaccinia topoisomerase enzyme. In another embodiment the vaccinia topoisomerase enzyme is a modified vaccinia topoisomerase enzyme. In a preferred embodiment the cleavage site comprises CCCTT. In another preferred embodiment the method further comprises introducing a biotin moiety or another affinity purification moiety, to the DNA cleavage substrate prior to step (a). In still another preferred embodiment the method further comprises immobilizing the affinity purification tagged DNA cleavage substrate on a solid support prior to step (a). In a preferred embodiment the solid support is a sepharose resin or magnetic beads having an affinity purification material, such as avidin, streptavidin, chitin, glutathione and the like, bound thereto. Methods of preparing such materials are well known in the art. In yet another preferred embodiment the method further comprises purifying a biotinylated 5' end tagged DNA-RNA ligation product by separating the solid support to which the biotinylated 5' end tagged DNA-RNA ligation product is immobilized from a liquid phase comprising unmodified RNA. In a preferred embodiment the 5' end of the DNA cleavage substrate is affinity labeled. In a preferred embodiment the affinity label is a biotin moiety. In another preferred embodiment the method further comprises immobilizing the biotinylated 5' end affinity labeled DNA cleavage substrate on a solid support. In a preferred embodiment the solid support is modified with streptavidin. In another preferred embodiment the method further comprises purifying the biotinylated 5' end affinity labeled DNA-RNA ligation product by separating the streptavidin-modified solid support to which the 5' end tagged DNA-RNA ligation product is immobilized from a liquid phase comprising unmodified RNA.

As used herein, unmodified RNA is defined as an RNA strand or strands which have not been joined covalently to a DNA strand.

The present invention provides a 5' end tagged RNA molecule. In a preferred embodiment of the 5' end tagged RNA molecule, the tag is a DNA sequence. In a further preferred embodiment the 5' end tagged RNA molecule further comprising a 5' end label. In an embodiment the 5' end label is $^{32}P$ or a radiohalogen. In another embodiment the 5' end label is a biotin moiety or another affinity purification moiety.

In an embodiment the 5' end tagging RNA molecule is generated by the above-described method of tagging a 5' end of an RNA molecule. In an embodiment the 5' end tagged RNA molecule further comprises a 5' end label. In a further embodiment the 5' end label is $^{32}P$. In another embodiment the 5' end label is a biotin moiety.

In another aspect the present invention further provides a DNA-RNA molecule which has been joined in vitro by the use of a topoisomerase.

As used herein the number of nucleotides (N) of the DNA cleavage substrate, designated supra as a DNA-(N) substrate, may be from one to four nucleotide(s) long.

The present invention also provides a method of tagging a 5' end of a capped messenger RNA comprising: a) isolating mRNA from cells or a tissue; b) removing an RNA cap structure from the isolated mRNA, resulting in a de-capped RNA; c) dephosphorylating the de-capped RNA, thereby forming a de-capped and dephosphorylated RNA; d) constructing a DNA cleavage substrate for topoisomerase having a topoisomerase cleavage site and a complementary strand, the complementary strand having a mixed or random base composition downstream of the topoisomerase cleavage site, the DNA cleavage substrate being designated as a DNA-(N) substrate; e) cleaving the DNA-(N) substrate with a topoisomerase, thereby forming a covalent topoisomerase-DNA-(N) complex containing a 5' tail of mixed or random base composition on a noncleaved strand; and f) incubating the cleaved covalent topoisomerase-DNA-(N) complex with the de-capped and dephosphorylated RNA formed in step (c) to form a 5' DNA-tagged DNA-RNA ligation product.

In an embodiment of the above-described method, the removal of the RNA cap structure is by either of enzymatic treatment of the mRNA with a pyrophosphatase or chemical decapping by periodate oxidation and beta elimination. In a preferred embodiment the pyrophosphatase is tobacco acid pyrophosphatase. In another preferred embodiment the topoisomerase cleavage site is CCCTT. In yet another preferred embodiment the DNA-(N) cleavage substrate has a biotin moiety upstream of the cleavage site and is designated BioDNA-(N). In an embodiment the method further comprises affinity purification of the biotinylated 5' DNA-tagged DNA-RNA ligation product by a binding of the biotin moiety to streptavidin prior to step (e).

The present invention also provides a 5' tagged DNA-RNA ligation product generated by the method of tagging a 5' end of a capped messenger RNA. In an embodiment the 5' tagged DNA-RNA ligation product further comprises a 5' end label. In a further embodiment of the 5' end tagged DNA-RNA ligation product, the label is $^{32}P$. In another embodiment of the 5' end tagged DNA-RNA ligation product, the label is a biotin moiety.

The present invention also provides a method of isolating and cloning a capped mRNA after subtraction of non-capped RNA comprising: a) isolating mRNA from cells or a tissue; b) dephosphorylating the mRNA; c) incubating a cleaved topoisomerase-BioDNA-(N) complex with the dephosphorylated mRNA to form a 5' BioDNA-tagged DNA-RNA ligation product; d) removing the 5' BioDNA-tagged DNA-RNA ligation product and any unreacted cleaved topoisomerase-BioDNA-(N) complex by adsorption to streptavidin and recovering any nonadsorbed material, said material being enriched for RNA having a capped 5' end and being resistant to dephosphorylation in step (b), thereby being unable to react with the cleaved topoisomerase-BioDNA-(N) complex; e) removing of the 5' end cap from the enriched RNA recovered from the nonadsorbed material in step (d); dephosphorylating the de-capped RNA, thereby forming a de-capped and dephosphorylated RNA; g) incubating a cleaved topoisomerase-BioDNA-(N) complex with the de-capped and dephosphorylated RNA to form a 5' BioDNA-tagged DNA-RNA ligation product; h) affinity purifying the 5' DNA-tagged DNA-RNA ligation product; and i) PCR amplification of the decapped and dephosphorylated RNA of the DNA-RNA ligation product using a sense primer corresponding to a scissile strand of the topoisomerase cleavage substrate 5' of the site of cleavage and an antisense primer, said antisense primer being complementary to either a 3' poly(A) tail or to an internal RNA sequence. In a preferred embodiment of the above-described method, the affinity purification in step (h) is by a binding of the 5' BioDNA-tagged DNA-RNA ligation product to streptavidin. In another preferred embodiment the removal of the RNA cap structure is by either of enzymatic treatment of the mRNA with a pyrophosphatase or chemical decapping by periodate oxidation and beta elimination. In yet another preferred embodiment the pyrophosphatase is tobacco acid pyrophosphatase.

In an embodiment of the method of covalently joining a DNA strand to an RNA strand, the 5' single strand tail has a specifically designed sequence.

Another aspect of the present invention provides a method of targeting ligation of an RNA strand of interest within a mixture of RNA strands which comprises the above-described method of covalently joining a DNA strand to an RNA strand. In an embodiment of the method of targeting ligation of an RNA strand of interest within a mixture of RNA strands which comprises the method of covalently joining a DNA strand to an RNA strand, the 5' single strand tail provides specificity of a covalently joined DNA-RNA ligation product.

In another preferred embodiment there is provided a method of obtaining a full-length gene sequence comprising: (a) isolating full-length mRNA; (b) attaching a DNA tag sequence to the isolated mRNA; and (c) synthesizing cDNA using the tagged mRNA as a template.

To insure that only full-length mRNA is used in this aspect of the invention (thus insuring the generation of a full-length gene sequence) it is generally preferred that only capped mRNA be isolated. Eukaryotic primary transcripts are modified at the initiating, or 5', nucleotide of the primary transcript by the addition of a 5' methylated cap (Shatkin, Cell 9:645, 1976) which may serve to protect the mRNA from enzymatic degradation. Only full-length transcripts will be so modified. The cap structure may be modified, such as by adding an affinity purification tag such as biotin, chitin binding domain, and the like (Carnici, et al, supra). The affinity tagged capped mRNA can then be isolated from degraded mRNA or RNAs with poly A tails that are not full-length coding mRNAs.

The affinity tagged mRNA can be separated from untagged RNA using affinity purification, for example by contacting the tagged mRNA with an affinity purification material such as a solid support complexed with streptavidin, avidin, chitin, glutathione, and the like. Alternatively, unmodified capped mRNA can be separated from RNA species lacking a cap by contacting the capped mRNA with a solid support complexed to, for example, phenylboronic acid (see Theus and Liarakos, Biotechniques 9(5):610-612, 1990). Suitable solid supports include various column chromatography gels, such as sepharose, agarose, and the like, and magnetic beads.

Any eukaryotic cell type can serve as a source for mRNA to be used in practicing the method of the invention including both animal cells and plant cells. Suitable animal cells include mammalian cells (rodent, non-human primate, primate, goat, sheep, cow, and the like) and insect cells (moth, *Drosophila*, and the like). Methods of extracting mRNA from different cell types are well known in the art (see, for example, Ausubel, et al, supra).

The isolated mRNA is preferably decapped and dephosphorylated after isolation. Methods of decapping RNAs are well known in the art and include both enzymatic methods (such as by using a pyrophosphatase such as tobacco pyrophosphatase) and chemical methods (such as periodate oxidation and beta elimination). Likewise methods for dephosphorylation of RNA are well known in the art, for example by using alkaline phosphatase.

Figure 11A:
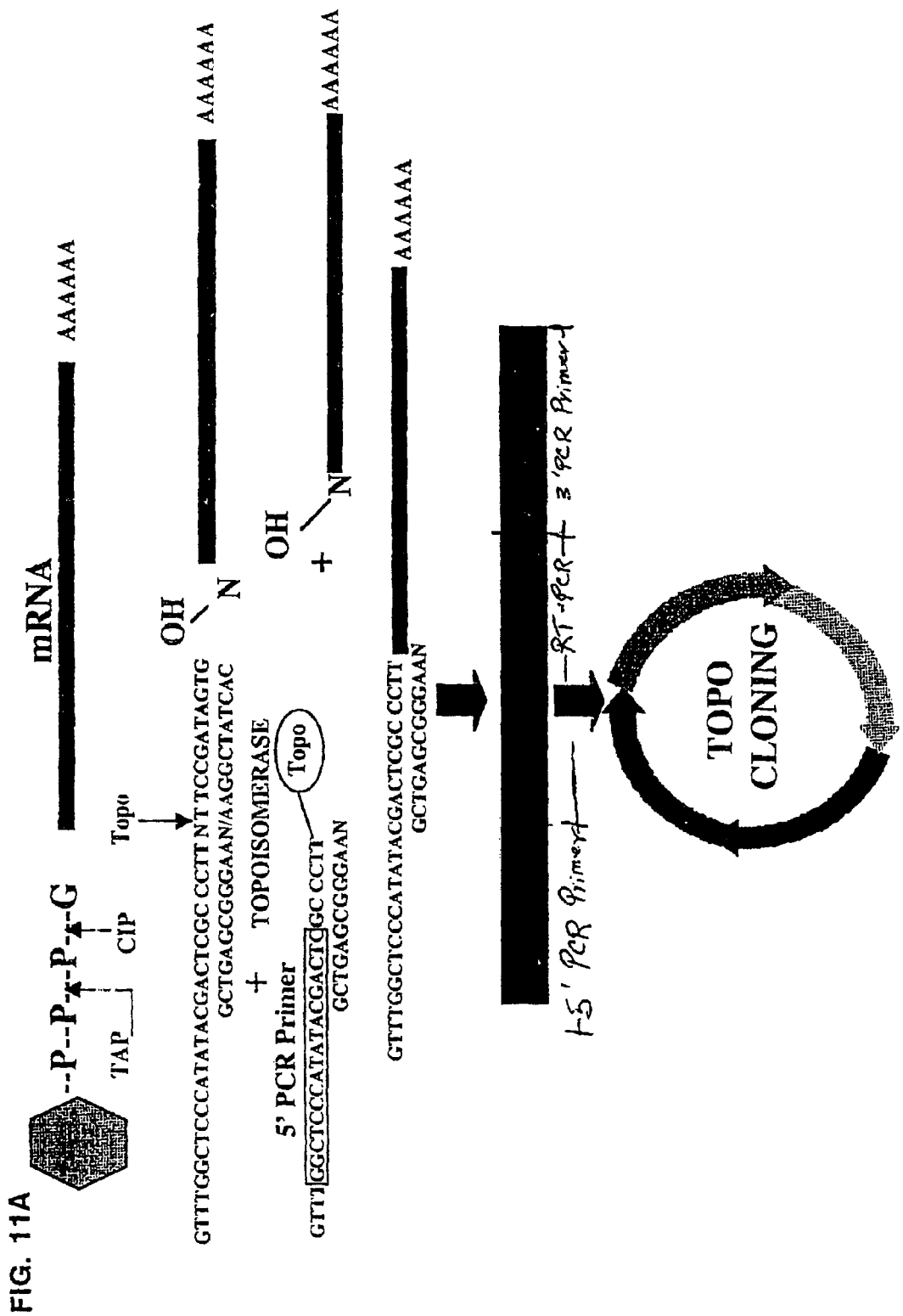
FIG. 11. (SEQ ID NOS: 28, 29, 30, and 31) A schematic representation of a method of using DNA-tagged mRNA to obtain full-length gene sequences. Briefly, capped full-length mRNA is isolated by attachment to a solid support, such as by using biotinylated-capped mRNA bound to a magnetic bead conjugated with streptavidin. The isolated mRNA is decapped (using tobacco acid pyrophosphatase) and dephosphorylated (using alkaline phosphatase) then modified with a DNA tag using the methods outlined below. The DNA-tagged mRNA is used to generate first strand cDNA using reverse transcriptase and amplified using PCR. The amplified cDNA is then inserted into a plasmid vector.
Figure 11B:
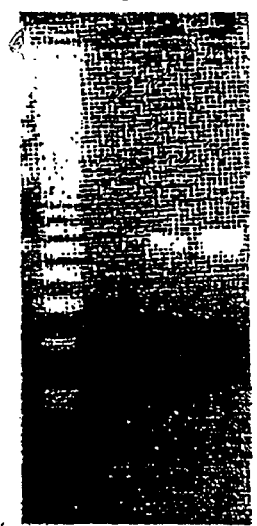
Figure 11C:
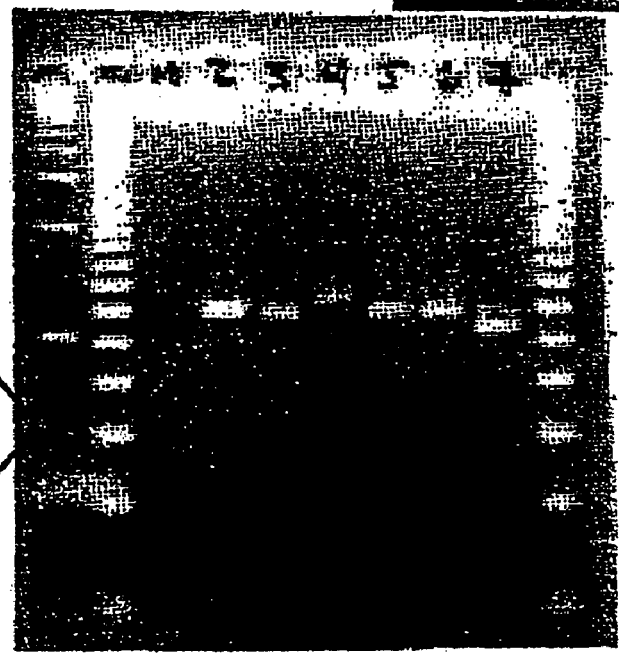

A DNA tag sequence can be attached to the isolated full-length mRNA using the methods described above. A preferred DNA tag sequence is shown in FIG. 11 both as a double stranded DNA cleavage substrate and as a covalent topoisomerase-DNA intermediate. The complementary strand of the topoisomerase-DNA intermediate includes a 3' overhang of from 1 to 4 nucleotides, which can be any mixture of adenine, guanine, cytosine or thymine, designated in the figure as N. These nucleotides will base pair with the first 1 to 4 bases of the 5' end of the isolated mRNA molecule, allowing the covalently attached topoisomerase to catalyze the transesterification reaction which joins the DNA tag to the end of the RNA sequence. The DNA tag sequence comprises a topoisomerase recognition site, preferably CCCTT, and in addition may comprise a recognition site for a site-specific restriction endonuclease, such as EcoRI, useful for the subsequent insertion of a cDNA molecule into an expression vector.

The DNA-RNA molecule is used as a template for synthesis and amplification of full-length cDNA sequences, preferably using the polymerase chain reaction (PCR), a technique well known in the art (see Ausubel, et al, supra). Suitable primers include all or a portion of the 5' tag sequence of the DNA-RNA molecule and a gene specific 3' primer or an oligo dT primer.

The amplified gene products are next isolated from the other components of the amplification reaction mixture. This purification can be accomplished using a variety of methodologies such as column chromatography, gel electrophoresis, and the like. A preferred method of purification utilizes low-melt agarose gel electrophoresis. The reaction mixture is separated and visualized by suitable means, such as ethidium bromide staining. DNA bands that represent correctly sized amplification products are cut away from the rest of the gel and placed into appropriate corresponding wells of a 96-well microtiter plate. These plugs are subsequently melted and the DNA contained therein utilized as cloning inserts.

The purified, amplified gene sequences are next inserted into an expression vector. A variety of expression vectors are suitable for use in the practice of the present invention, both for prokaryotic expression and eukaryotic expression. In general, the expression vector will have one or more of the following features: a promoter-enhancer sequence, a selection marker sequence, an origin of replication, an affinity purification tag sequence, an inducible element sequence, an epitope-tag sequence, and the like.

Promoter-enhancer sequences are DNA sequences to which RNA polymerase binds and initiates transcription. The promoter determines the polarity of the transcript by specifying which strand will be transcribed. Bacterial promoters consist of consensus sequences, −35 and −10 nucleotides relative to the transcriptional start, which are bound by a specific sigma factor and RNA polymerase. Eukaryotic promoters are more complex. Most promoters utilized in expression vectors are transcribed by RNA polymerase II. General transcription factors (GTFs) first bind specific sequences near the start and then recruit the binding of RNA polymerase II. In addition to these minimal promoter elements, small sequence elements are recognized specifically by modular DNA-binding/trans-activating proteins (eg. AP-1, SP-1) which regulate the activity of a given promoter. Viral promoters serve the same function as bacterial or eukaryotic promoters and either provide a specific RNA polymerase in trans (bacteriophage T7) or recruit cellular factors and RNA polymerase (SV40, RSV, CMV). Viral promoters are preferred as they are generally particularly strong promoters.

Promoters may be, furthermore, either constitutive or, more preferably, regulatable (i.e., inducible or derepressible). Inducible elements are DNA sequence elements which act in conjunction with promoters and bind either repressors (eg. lacO/LAC Iq repressor system in *E. coli*) or inducers (eg. gall/GAL4 inducer system in yeast). In either case, transcription is virtually "shut off" until the promoter is derepressed or induced, at which point transcription is "turned-on".

Examples of constitutive promoters include the int promoter of bacteriophage λ, the bla promoter of the β-lactamase gene sequence of pBR322, the CAT promoter of the chloramphenicol acetyl transferase gene sequence of pPR325, and the like. Examples of inducible prokaryotic promoters include the major right and left promoters of bacteriophage ($P_L$ and $P_R$), the trp, reca, lacZ, LacI, AraC and gal promoters of *E. coli*, the α-amylase (Ulmanen Ett at., J. Bacteriol. 162:176-182, 1985) and the sigma-28-specific promoters of *B. subtilis* (Gilman et al., Gene sequence 32:11-20 (1984)), the promoters of the bacteriophages of *Bacillus* (Gryczan, In: The Molecular Biology of the Bacilli, Academic Press, Inc., NY (1982)), *Streptomyces* promoters (Ward et at., Mol. Gen. Genet. 203:468-478, 1986), and the like. Exemplary prokaryotic promoters are reviewed by Glick (J. Ind. Microtiot. 1:277-282, 1987); Cenatiempo (Biochimie 68:505-516, 1986); and Gottesman (Ann. Rev. Genet. 18:415-442, 1984).

Preferred eukaryotic promoters include, for example, the promoter of the mouse metallothionein I gene sequence (Hamer et al., J. Mol. Appl. Gen. 1:273-288, 1982); the TK promoter of Herpes virus (McKnight, Cell 31:355-365, 1982); the SV40 early promoter (Benoist et al., Nature (London) 290:304-310, 1981); the yeast gall gene sequence promoter (Johnston et al., Proc. Natl. Acad. Sci. (USA) 79:6971-6975, 1982); Silver et al., Proc. Natl. Acad. Sci. (USA) 81:5951-5955, 1984), the CMV promoter, the EF-1 promoter, Ecdysone-responsive promoter(s), and the like.

Selection marker sequences are valuable elements in expression vectors as they provide a means to select, for growth, only those cells which contain a vector. Such markers are of two types: drug resistance and auxotrophic. A drug resistance marker enables cells to detoxify an exogenously added drug that would otherwise kill the cell. Auxotrophic markers allow cells to synthesize an essential component (usually an amino acid) while grown in media which lacks that essential component.

Common selectable marker gene sequences include those for resistance to antibiotics such as ampicillin, tetracycline, kannamycin, bleomycin, streptomycin, hygromycin, neomycin, Zeocin™, and the like. Selectable auxotrophic gene sequences include, for example, hisD, which allows growth in histidine free media in the presence of histidinol.

A preferred selectable marker sequence for use in yeast expression systems is URA3. Laboratory yeast strains carrying mutations in the gene which encodes orotidine-5'-phosphate decarboxylase, an enzyme essential for uracil biosynthesis, are unable to grow in the absence of exogenous uracil. A copy of the wild-type gene (ura4+ in *S. pombe* and URA3 in *S. cerevisiae*) will complement this defect in trans.

A further element useful in an expression vector is an origin of replication sequence. Replication origins are unique DNA segments that contain multiple short repeated sequences that are recognized by multimeric origin-binding proteins and which play a key role in assembling DNA replication enzymes at the origin site. Suitable origins of replication for use in expression vectors employed herein include *E. coli* oriC, 2µ and ARS (both useful in yeast systems), sf1, SV40 (useful in mammalian systems), and the like.

Additional elements that can be included in an expression vector employed in accordance with the present invention are sequences encoding affinity purification tags or epitope tags. Affinity purification tags are generally peptide sequences that can interact with a binding partner immobilized on a solid support. Synthetic DNA sequences encoding multiple consecutive single amino acids, such as histidine, when fused to the expressed protein, may be used for one-step purification of the recombinant protein by high affinity binding to a resin column, such as nickel sepharose. An endopeptidase recognition sequence can be engineered between the polyamino acid tag and the protein of interest to allow subsequent removal of the leader peptide by digestion with Enterokinase, and other proteases. Sequences encoding peptides such as the chitin binding domain (which binds to chitin), glutathione-S-transferase (which binds to glutathione), biotin (which binds to avidin and strepavidin), and the like can also be used for facilitating purification of the protein of interest. The affinity purification tag can be separated from the protein of interest by methods well known in the art, including the use of inteins (protein self-splicing elements, Chong, et al, Gene 192:271-281, 1997).

Epitope tags are short peptide sequences that are recognized by epitope specific antibodies. A fusion protein comprising a recombinant protein and an epitope tag can be simply and easily purified using an antibody bound to a chromatography resin. The presence of the epitope tag furthermore allows the recombinant protein to be detected in subsequent assays, such as Western blots, without having to produce an antibody specific for the recombinant protein itself. Examples of commonly used epitope tags include V5, glutathione-S-transferase (GST), hemaglutinin (HA), the peptide Phe-His-His-Thr-Thr (SEQ ID NO: 46), chitin binding domain, and the like.

A further useful element in an expression vector is a multiple cloning site or polylinker. Synthetic DNA encoding a series of restriction endonuclease recognition sites is inserted into a plasmid vector downstream of the promoter element. These sites are engineered for convenient cloning of DNA into the vector at a specific position.

The foregoing elements can be combined to produce expression vectors useful in creating the libraries of the invention. Suitable prokaryotic vectors include plasmids such as those capable of replication in *E. coli* (for example, pBR322, ColE1, pSC101, PACYC 184, itVX, pRSET, pBAD (Invitrogen, Carlsbad, Calif.) and the like). Such plasmids are disclosed by Sambrook (cf. "Molecular Cloning: A Laboratory Manual", second edition, edited by Sambrook, Fritsch, & Maniatis, Cold Spring Harbor. Laboratory, (1989)). *Bacillus* plasmids include pC194, pC221, pT127, and the like, and are disclosed by Gryczan (In: The Molecular Biology of the Bacilli, Academic Press, NY (1982), pp. 307-329). Suitable *Streptomyces* plasmids include plJ101 (Kendall et al., J. Bacteriol. 169:4177-4183, 1987), and *streptomyces* bacteriophages such as φC31 (Chater et al., In: Sixth International Symposium on Actinomycetales Biology, Akademiai Kaido, Budapest, Hungary (1986), pp. 45-54). *Pseudomonas* plasmids are reviewed by John et al. (Rev. Infect. Dis. 8:693-704, 1986), and Izaki (Jpn. J. Bacteriol. 33:729-742, 1978).

Suitable eukaryotic plasmids include, for example, BPV, vaccinia, SV40, 2-micron circle, pcDNA3.1, pcDNA3.1/GS, pYES2/GS, pMT, p IND, pIND(Sp1), pVgRXR (Invitrogen), and the like, or their derivatives. Such plasmids are well known in the art (Botstein et al., Miami Wntr. Symp. 19:265-274, 1982; Broach, In: "The Molecular Biology of the Yeast *Saccharomyces*: Life Cycle and Inheritance", Cold Spring Harbor Laboratory, Cold Spring Harbor, N.Y., p. 445-470, 1981; Broach, Cell 28:203-204, 1982; Dilon et at., J. Clin. Hematol. Oncol. 10:39-48, 1980; Maniatis, In: Cell Biology: A Comprehensive Treatise, Vol. 3, Gene Sequence Expression, Academic Press, NY, pp. 563-608, 1980.

Once plasmids containing the gene sequence insert in the correct orientation have been identified, plasmid DNA is prepared for use in the transformation of host cells for expression. Methods of preparing plasmid DNA and transformation of cells are well known to those skilled in the art. Such methods are described, for example, in Ausubel, et al, supra.

Prokaryotic hosts are, generally, very efficient and convenient for the production of recombinant proteins and are, therefore, one type of preferred expression system. Prokaryotes most frequently are represented by various strains of *E. coli*. However, other organisms may also be used, including other bacterial strains.

Recognized prokaryotic hosts include bacteria such as *E. coli* and those from genera such as *Bacillus, Streptomyces, Pseudomonas, Salmonella, Serratia*, and the like. However, under such conditions, the polypeptide will not be glycosylated. The prokaryotic host selected for use herein must be compatible with the replicon and control sequences in the expression plasmid.

Suitable hosts may often include eukaryotic cells. Preferred eukaryotic hosts include, for example, yeast, fungi, insect cells, and mammalian cells either in vivo, or in tissue culture. Mammalian cells which may be useful as hosts include HeLa cells, cells of fibroblast origin such as VERO, 3T3 or CHOK1, HEK 293 cells or cells of lymphoid origin (such as 32D cells) and their derivatives. Preferred mammalian host cells include nonadherent cells such as CHO, 32D, and the like. Preferred yeast host cells include *S. pombe, Pichia pastoris, S. cerevisiae* (such as INVSc1), and the like.

In addition, plant cells are also available as hosts, and control sequences compatible with plant cells are available, such as the cauliflower mosaic virus 35S and 19S, nopaline synthase promoter and polyadenylation signal sequences, and the like. Another preferred host is an insect cell, for example the *Drosophila* larvae. Using insect cells as hosts, the *Drosophila* alcohol dehydrogenase promoter can be used. Rubin, Science 240:1453-1459, 1988). Alternatively, baculovirus vectors can be engineered to express large amounts of peptide encoded by a desire gene sequence in insects cells (Jasny, Science 238:1653, 1987); Miller et al., In: Genetic Engineering (1986), Setlow, J. K., et al., eds., Plenum, Vol. 8, pp. 277-297). The present invention also features the purified, isolated or enriched versions of the expressed gene products produced by the methods described above.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Methods and Materials

Preparation of Tandem RNA-p-DNA and DNA-p-RNA Oligonucleotides.

CCCTT-containing 36-mer oligonucleotides containing a single internal $^{32}$P-label at the scissile phosphate were prepared by ligating two 18-mer strands (synthetic RNA or DNA oligonucleotides) that had been hybridized to a complementary 36-mer DNA strand. The sequence of the proximal CCCTT-containing 18-mer strand was 5'-CATATCCGT-GTCGCCCTT (SEQ ID NO: 3) as DNA or 5'-CAUAUC-CGUGUCCCUU (SEQ ID NO: 47) as RNA. The sequence of the distal 18-mer strand was 5'-ATTCCGATAGTGACTACA (SEQ ID NO: 4) as DNA or 5'-AUUCCGAUAGUGAC-UACA (SEQ ID NO: 48) as RNA. The distal 18-mer strand was 5'-labeled in the presence of $[\gamma^{32}P]$ ATP and T4 polynucleotide kinase, then gel-purified. The sequence of the 36-mer strand was 5'-TGTAGTCACTATCG-GAATAAGGGCGACACGGATATG (SEQ ID NO: 5). The strands were annealed in 0.2 M NaCl by heating at 65° C. for 2 min, followed by slow-cooling to room temperature. The molar ratio of the 5'-labeled distal 18-mer to the proximal 18-mer and the 36-mer strand in the hybridization mixture was 1:4:4. The singly nicked product of the annealing reaction was sealed in vitro with purified recombinant vaccinia virus DNA ligase (14, 15). The ligation reaction mixtures (400 ul) contained 50 mM Tris HCl (pH 8.0), 5 mM DTT 10 mM MnC12, 1 mM ATP, 10 pmol of 5' $^{32}$$_p$-labeled nicked substrate, and 160 pmol of ligase. After incubation for 4 h at 22° C., the reactions were halted by the addition of EDTA to a final concentration of 25 mM. The samples were extracted with phenol-chloroform and the labeled nucleic acid was recovered from the aqueous phase by ethanol precipitation. The 36-mer duplex products were dissolved in TE buffer (10 mM tris HCl, pH 8.0, 1 mM EDTA). Ligation of the labeled 18-mer distal strand to the unlabeled CCCTT-containing 18-mer strand to form an internally labeled 36-mer product was confirmed by electrophoresis of the reaction products through a 17% denaturing polyacrylamide gel. The extents of ligation [36-men/(36-mer+18-mer)] were as follows: DNA-p-DNA (88%); DNA-p-RNA (67%); RNA-p-DNA (66%).

Covalent Binding of Topoisomerase to Internally Labeled 36-Mer Duplexes.

Recombinant vaccinia topoisomerase was expressed in bacteria and purified via phosphocellulose and SP5PW column chromatography as described (16, 17). Reaction mixtures for assay of covalent adduct formation contained (per 20 µl) 50 mM Tris-HCl (pH 8.0), 0.2 pmol of 36-mer duplex, and 1 pmol of topoisomerase. The reactions were initiated by adding topoisomerase and halted by adding SDS to 1% final concentration. the samples were analyzed by SDS-PAGE. Covalent complex formation was revealed by the transfer of radiolabeled polynucleotide to the topoisomerase polypeptide (3). The extent of adduct formation was quantitated by scanning the gel using a FUJIX BAS1000 phosphorimager and was expressed as the percent of the input 5' $^{32}$P-labeled 36-mer substrate that was covalently transferred to protein.
DNA Strand Transfer to an RNA Acceptor.

An 18-mer CCCTT-containing DNA oligonucleotide (5'-CGTGTCGCCCTTATTCCC) (SEQ ID NO: 19) was 5'end-labeled in the presence of [γ 32p] ATP and T4 polynucleotide kinase, then gel-purified and hybridized to a complementary 30-mer strand to form the 18-mer/30-mer suicide cleavage substrate. Covalent topoisomerase-DNA complexes were formed in a reaction mixture containing (per 20 ul) 50 mM Tris-HCl (pH 8.0), 0.5 pmol of 18-mer/30-mer DNA, and 2.5 pmol of topoisomerase. The mixture was incubated for 5 min at 37° C. The strand transfer reaction was initiated by adding an 18-mer acceptor strand 5'-ATTCCGATAGTGACTACA (SEQ ID NO: 8) (either DNA or RNA) to a concentration of 25 pmol/20 pi (i.e., a 50-fold molar excess over the input DNA substrate), while simultaneously adjusting the reaction mixtures to 0.3 M NaCl. The reactions were halted by addition of SDS and formamide to 0.2% and 50%, respectively. The samples were heat-denatured and then electrophoresed through a 17 polyacrylamide containing 7 M urea in TBE (90 mM Tris-borate, 2.5 mM EDTA). The extent of strand transfer (expressed as the percent of input labeled DNA converted to a 30-mer strand transfer product) was quantitated by scanning the wet gel with a phosphorimager.
Preparation of $^{32}$P-Labeled 36-mer RNA.

A 36-nucleotide run-off transcript was synthesized in vitro by T3 RNA polymerase from a pBluescript II-SK(−) plasmid template that had been linearized by digestion with endonuclease EagI. A transcription reaction mixture (100 µl) containing 40 mM Tris HCl (pH 8.0), 6 mM $MgCl_2$, 2 mM spermidine, 10 mM NaCl, 10 mM DTT, 0.5 mM ATP, 0.5 mM CTP, 0.5 mM UTP, 6.25 µM $[\alpha^{32}P]$ GTP, 5 µg of template DNA, and 100 units of T3 RNA polymerase (Promega) was incubated for 90 min at 37° C. The reaction was halted by adjusting the mixture to 0:1% SDS, 10 mM EDTA, and 0.5 M ammonium acetate. The samples were extracted with phenol-chloroform and ethanol-precipitated. The pellet was resuspended in formamide and electrophoresed through a 12% polyacrylamide gel containing 7M urea in TBE. The radiolabeled 36-mer RNA was localized by autoradiography of the wet gel and eluted from an excised gel slice by soaking for 16 h at 4° C. in 0.4 ml of buffer containing 1 M ammonium acetate, 0.2% SDS, and 20 mM EDTA. The eluate was phenol-extracted and ethanol-precipitated. The RNA was resuspended in TE. Dephosphorylation of the RNA 5' terminus was carried out in a reaction mixture (30 μl) containing 10 mM Tris HCl (pH 7.9), 50 mM NaCl, 10 mM $MgCl_2$, 1 mM DTT, 10 pmol of 36-mer RNA, and 30 units of calf intestine alkaline phosphatase (New England Biolabs). After a 1 h incubation at 37° C., the mixture was phenol-extracted and ethanol-precipitated. The phosphatase-treated 36-mer transcript was repurified electrophoretically as described above.

Affinity Tagging of RNA Using Vaccinia Topoisomerase

Figure 10A:
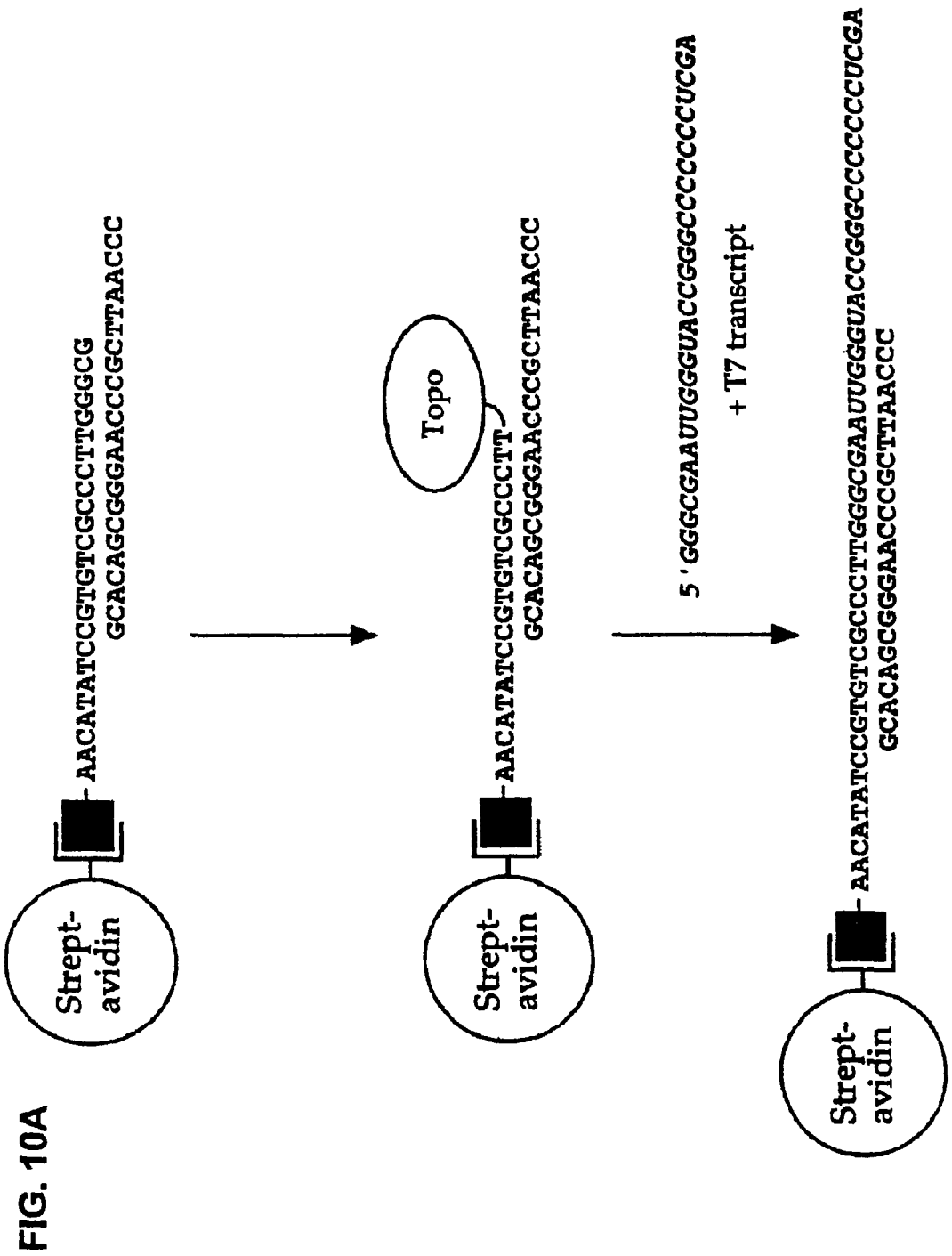

The strand transfer reaction pathway is diagrammed in FIG. 10a. The biotinylated DNA Substrate which contains a single topoisomerase recognition site is immobilized on the Dynabeads (Dynal) streptavidin solid support. The biotin moiety (indicated by the black square) is introduced at the 5' end of the CCCTT-containing strand via standard protocols for automated oligonucleotide synthesis. The purified vaccinia topoisomerase is reacted with the bead-bound DNA to form a covalent enzyme-DNA donor complex, as illustrated. Enzyme not bound to DNA is removed by washing the beads with buffer. The strand transfer reaction is initiated by addition of the [$^{32}$P]-CMP labeled T7 transcript which is dephosphorylated by prior treatment with alkaline phosphatase. The 5' single-strand tail of the donor complex is complementary to the 12 nucleotides at the 5' end of the T7 transcript. Religation of the covalently held biotinylated DNA strand to the T7 transcript is observed as conversion of the 30-mer RNA to a product of 50 nucleotides.

Experimental Details: The DNA substrate was formed by annealing the biotinylated 25-mer strand containing the topoisomerase recognition site to a complementary 5' phosphorylated 24-mer strand (present at a 4-fold molar excess). The strands were annealed in the presence of 0.2 M NaCl by heating at 65° C. for 10 min, followed by slow cooling to room temperature. The biotinylated duplex was immobilized on streptavidin beads by incubating 10 pmol of the DNA with 10 μg of Dynabeads in 50 mM Tris-HCl (pH 8.0), 1 M NaCl for 10 min at 22° C. The beads were recovered by centrifugation. The beads were rinsed twice with 1 ml of 50 mM Tris-HCl (pH 8.0). The washed beads were resuspended in 20 μl of 50 mM Tris-HCl (pH 8.0). A 5-fold molar excess of topoisomerase (50 pmol) was added to the bead-linked DNA substrate. The mixture was incubated at 37° C. for min. The beads were recovered by centrifugation, rinsed twice with 1 ml of 50 mM Tris-HCl, then resuspended in 18 μl of 50 mM Tris-HCl, 0.3 M NaCl. Strand transfer was initiated by addition of 1 pmol of [$^{32}$P]-CMP labeled T7 transcript. The mixture was incubated at 37° C. for 15 min. The beads were then recovered by centrifugation, washed, and resuspended in 20 μl of buffer containing 0.8% SDS and 80% formamide. The samples were heated at 95° C. for 5 min, centrifuged for 5 min, then the supernatants were electrophoresed through a 12% polyacrylamide gel containing 7M urea in TBE buffer. An autoradiograph of the gel is shown in FIG. 10B. Lane B (Bound)—product of the strand transfer reaction bound to the Dynabeads; lane F (Free)—supernatant from the strand transfer reaction. The positions of the input 30-mer T7 transcript and the 50-mer product are shown at the right.

RNA substrate: The 30-nucleotide runoff transcript was synthesized in vitro by T7 RNA polymerase from a pBluescript II-SK(−) plasmid template that had been linearized by digestion with endonuclease XhoI. The transcript was labeled with [$\alpha^{32}$P]-CTP under similar reaction conditions as described for preparation of the T3 RNA transcript. The 30-mer RNA was gel-purified and subsequently dephosphorylated as described.

Results

Covalent Binding of Topoisomerase to a Duplex Substrate Containing RNA 3' of the Scissile Phosphate.

Figure 1B:
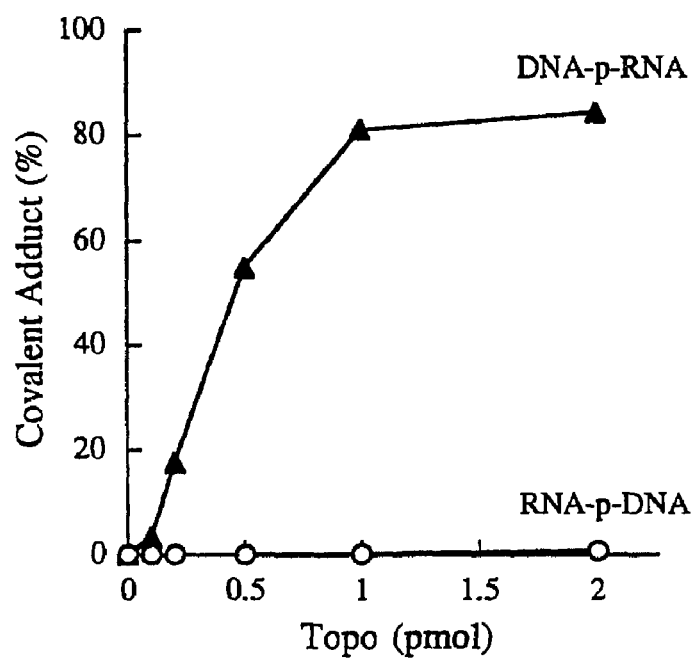

Vaccinia topoisomerase does not bind covalently to CCCTT-containing RNA duplexes; nor does it form a covalent complex on RNA-DNA hybrid duplexes in which one of the two strands is RNA (9). Control experiments showed that the failure to form a covalent adduct on a CCCUU-containing RNA strand was not caused by uracil substitution for the thymine bases in the CCCTT sequence (9). To better understand why vaccinia topoisomerase does not form a covalent complex with all-RNA strands, we prepared 36-bp duplex substrates in which the scissile strand was a tandem RNA-DMA or DNA-RNA copolymer and the noncleaved strand was all-DNA (FIG. 1). These duplexes were uniquely labeled with $^{32}$P at the scissile phosphodiester. The substrate molecules were constructed by annealing two 18-mer oligonucleotides (one of which had been 5' $^{32}$P-labeled) to a complementary 36-mer DNA strand to form a singly nicked duplex. The 5'-labeled 18-mer strand was then joined to the unlabeled CCCTT-strand (or CCCUU strand) in a reaction catalyzed by vaccinia virus DNA ligase. The 36-mer duplex products were isolated and then used as substrates for vaccinia DNA topoisomerase. We will refer to these substrates as DNA-p-DNA, DNA-p-RNA, and RNA-p-DNA, with the labeled phosphate being denoted by p.

Transesterification by topoisomerase at the CCCTT site will result in covalent binding of a 3' $^{32}$P-labeled 18-mer oligonucleotide to the enzyme. The extent of covalent complex formation on the DNA-p-RNA substrate in 10 min was proportional to input topoisomerase; 80-85% of the 36-mer strand was transferred to the topoisomerase at saturating enzyme (FIG. 1). The same level of topoisomerase covalently bound less than 1% of the RNA-p-DNA 36-mer strand. Hence, the topoisomerase tolerated RNA substitution downstream of the scissile phosphate, but was impeded from forming the covalent adduct when the CCCTT sequence was in RNA form.

The kinetics of the covalent binding reaction at a saturating level of topoisomerase were assessed (FIG. 2). An all-DNA 36-mer (DNA-p-DNA) was bound to an endpoint of 21% in 2 min (FIG. 2A). The apparent cleavage-religation equilibrium constant ($K_{cl}$—covalent complex/noncovalent complex) was 0.26, which agrees with values of 0.2 to 0.25 reported previously for equilibrium cleavage of a 5' end-labeled CCCTT-containing DNA substrate (10, 11). The DNA-p-RNA 36-mer was bound covalently to an endpoint of 80% in 5 min (FIG. 2A, and other data not shown). The apparent equilibrium constant for DNA-p-RNA ($K_{Cl}$=4) was significantly higher than that observed for the all-DNA ligand.

The RNA-p-DNA 36-mer was transferred to the topoisomerase, albeit very slowly. After 4 h, 4% of the CCCUU-containing RNA strand was bound covalently to the enzyme (FIG. 2B). An endpoint was not established in this experiment. However, by comparing the initial rate of covalent adduct formation on RNA-p-DNA (0.04% of input substrate cleaved per min) to the amount adduct formed on DNA-p-DNA at the earliest timepoint (12% in 10 sec), it is estimated that RNA substitution of the CCCTT-portion of the substrate slowed the rate of covalent complex formation by about three orders of magnitude.

DNA Strand Transfer to an RNA Acceptor.

Figure 4:
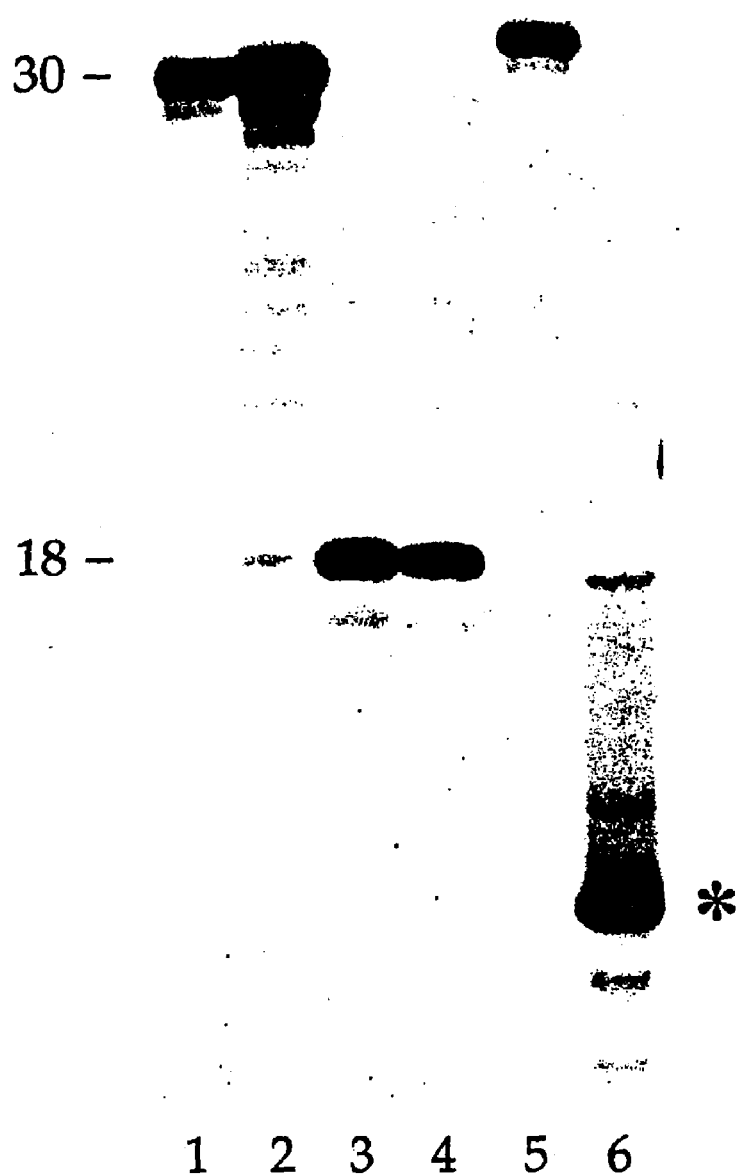
FIG. 4. Analysis of the strand transfer reaction products. Reaction mixtures (20 µl) containing 50 mM Tris-HCl (pH 8.0), 0.5 pmol of 5'-labeled suicide DNA cleavage substrate, and 2.5 pmol of topoisomerase were incubated at 37° C. for 10 min. Strand transfer was then initiated by adding a 50-fold excess of the acceptor DNA (18-mer D; lanes 1 and 2) or acceptor RNA (18-mer R; lanes 5 and 6), while simultaneously adjusting the mixtures to 0.3 M NaCl. The religation reactions were quenched after a 10 min incubation by adding SDS to 0.2%. The samples were extracted with phenol/chloroform and ethanol-precipitated. The pellets were resuspended in either 12 µl of 0.1M NaOH, 1 mM EDTA (NaOH +) or 12 µl of 10 mM Tris-HCl (pH 8.0), 1 mM EDTA (NaOH −). These samples were incubated at 37° C. for 16 h. Control samples containing the input 18-mer DNA substrate that had not been exposed to topoisomerase were treated in parallel (lanes 3 and 4). The alkali-treated samples were neutralized by adding 1.2 µl of 1 M HCl. All samples were then ethanol-precipitated, resuspended in formamide, heated for 5 min at 95° C., and then electrophoresed through a 17% polyacrylamide gel containing 7 M urea in TBE. An autoradiograph of the gel is shown. The positions of the 30-mer religation product and the 18-mer input strand are indicated at the left. Alkaline hydrolysis of the RNA strand transfer reaction product (lane 6) yielded a discrete species denoted by the asterisk.

Rejoining of the cleaved strand occurs by attack of a 5' hydroxyl terminated polynucleotide on the 3'phosphodiester bond between Tyr-274 and the CCCTT site. This transesterification step can be studied independent of strand cleavage by assaying the ability of a performed topoisomerase-DNA complex to religate the covalently held strand to a heterologous acceptor strand (5, 11). To form the covalent topoisomerase-DNA donor complex, the enzyme was initially incubated with a suicide substrate consisting of a 5'$^{32}$P-labeled 18-mer scissile strand (CGTGTCGCCCTTATTCCC) (SEQ ID NO: 19) hybridized to a 30-mer strand. With no readily available acceptor for religation, the enzyme is essentially trapped on the DNA as a suicide intermediate (FIG. 3). In a 5 min reaction in enzyme excess, >90% of the 5'$^{32}$P-labeled strand becomes covalently bound to protein. The strand transfer reaction was initiated by adding a 50-fold molar excess of an 18-mer acceptor strand (either DNA or RNA) complementary to the 5' single-strand tail of the covalent donor complex (FIG. 3), while simultaneously increasing the ionic strength to 0.3 M NaCl. Addition of NaCl during the religation phase promotes dissociation of the topoisomerase after strand closure and prevents recleavage of the strand transfer product. Ligation of the covalently held 12-mer CGTGTCGCCCTT (SEQ ID NO: 6) to the 18-mer yields a $^{32}$P-labeled 30 mer (FIG. 4, lane 1). The suicide intermediate transferred 94% of the input CCCTT-containing strand to the 18-mer DNA strand (FIG. 3). The extent of religation at the earliest time point (5 sec) was 90% of the endpoint value. From this datum a religation rate constant (krel) of >0.5 sec—was calculated. A krel value of ~1.3 sec$^{-1}$ had been determined previously (from experimental values for k, and at 37° C.) (18).

Topoisomerase readily ligated the covalently held 12-mer DNA to an 18-mer RNA acceptor to form a 30-mer product (FIG. 4, lane 5). 89% of the input CCCTT-strand was transferred to RNA, with 40% of the endpoint value attained in 5 sec. This datum was used to estimate a rate constant of 0.1 sec$^{-1}$ for single-turnover strand transfer to RNA. Thus, religation to DNA was about 10 times faster than religation to RNA. The slowed rate of RNA religation is likely to account for the observed increase in the cleavage-religation equilibrium constant ($K_{eq}=k_{cl}/k_{rel}$) on the DNA-p-RNA 36-mer.

Analysis of the Strand Transfer Reaction Product

The predicted product of strand transfer to RNA is a 30-mer tandem DNA-RNA strand (5'-CGTGTCGCCCTTA-UUCCGAUAGUGACUACA) (SEQ ID NO: 36) uniquely 32P-labeled at the 5'end. The structure of this molecule was confirmed by analysis of the susceptibility of this product to treatment with NaOH. The labeled 30-mer RNA ligation product was converted nearly quantitatively into a discrete species that migrated more rapidly than the input 18-mer CCCTT-containing DNA strand (FIG. 4 lane 6). The mobility of this product was consistent with a chain length of 13 nucleotides. The expected $^{32}$p-labeled alkaline hydrolysis product of the RNA strand transfer product is a 13-mer (5'-CGTGTCGCCCTTAp) (SEQ ID NO: 37). Control reactions showed that neither the $^{32}$P-labeled 18-mer scissile strand of the suicide substrate nor the 30-mer product of strand transfer to DNA was susceptible to alkali (FIG. 4, lanes 4 and 2). It is concluded that topoisomerase can be used to ligate RNA to DNA in vitro.

DNA ligand Tagging of an RNA Transcript Synthesized In Vitro by T3 RNA Polymerase.

Practical applications of topoisomerase-mediated strand transfer to RNA include the 5' tagging of RNA transcripts. Bacteriophage RNA polymerases have been used widely to synthesize RNA polymerases have been used widely to synthesize RNA in vitro from plasmid DNA templates containing phase promoters. To test whether such transcripts were substrates for topoisomerase-catalyzed ligation, we constructed a CCCTT-containing suicide cleavage substrate that, when cleaved by topoisomerase, would contain a 5' single-strand tail complementary to the predicted 5' sequence of any RNA transcribed by T3 RNA polymerase from a pBluescript vector (FIG. 5). A 36-nucleotide T3 transcript was synthesized in a transcription reaction containing [$\alpha^{32}$P] GTP. The RNA was treated with alkaline phosphatase to dephosphorylate the 5' terminus. The topoisomerase-DNA covalent intermediate was formed on an unlabeled suicide substrate. Incubation of the radiolabeled T3 transcript with the suicide intermediate resulted in the conversion of the 36-mer RNA into a novel species that migrated more slowly during polyacrylamide gel electrophoresis (not shown). The apparent size of this product (48 nucleotides) was indicative of ligation to the 12-mer CCCTT DNA strand. The kinetics of DNA ligation to the T3 transcript are shown in FIG. 5. The reaction was virtually complete within 1 min; at its endpoint 29% of the input RNA had been joined to DNA. No DNA-RNA ligation product was formed in reaction containing a T3 transcript that had not been treated with alkaline phosphatase (not shown).

Formation of Insertions and Deletions—A Kinetic Analysis.

The acceptor polynucleotides used in the experiments described above were capable of hybridizing perfectly with the 5' single-strand tail of the topoisomerase-DNA donor complex. It had been shown previously that the vaccinia virus topoisomerase is capable of joining the CCCTT-strand to an acceptor oligonucleotide that hybridizes so as to leave a single nucleotide gap between the covalently bound donor 3' end and the 5' terminus of the acceptor. Religation across this gap generated a 1 base deletion in enzyme also catalyzes strand transfer to an acceptor oligonucleotide that, when hybridized, introduces an extra nucleotide between the donor 3' end and the penultimate base-paired nucleotide of the acceptor. Religation in this case will produce a 1 base insertion (5). Deletion and insertion formation in vitro have also been documented for mammalian type I topoisomerase (19). However, there has been no report of the effects of acceptor strand gaps and insertions on the rate of strand joining by these enzymes.

Figure 7:
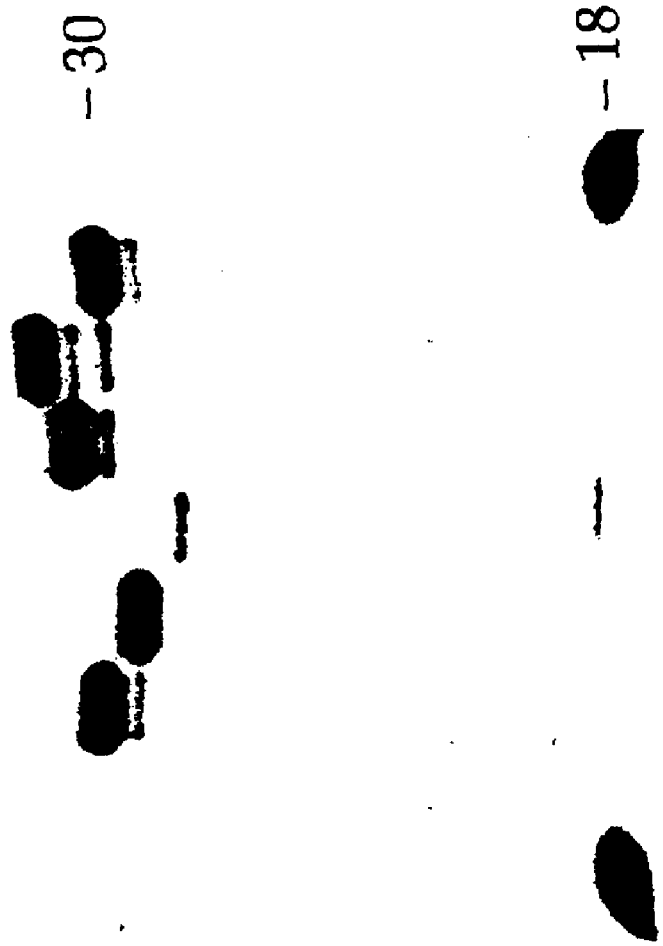
FIG. 7. Analysis of deleted and inserted DNA strand transfer products. Religation to acceptors with recessed and protruding 5' ends was performed as described in the legend to FIG. 6. The reaction products were analyzed by electrophoresis through a 17% polyacrylamide gel containing 7 M urea in TBE. An autoradiograph of the gel is shown. The acceptor strands were as follows: no acceptor (lane 2); perfectly paired 18-mer (lanes 3 and 8); 17-mer with a 1-nucleotide gap (lane 4); 16-mer with a 2-nucleotide gap (lane 5); 19-mer with a 1-nucleotide insert (lane 6); 20-mer with a 2-nucleotide insert (lane 7). Control samples containing the 5'-labeled 18-mer scissile strand but no topoisomerase were analyzed in lanes 1 and 9.

The kinetics of strand transfer by the vaccinia topoisomerase covalent intermediate to acceptor oligonucleotides that base-pair to the donor complex to form either a fully base-paired 3' duplex segment, or 3' duplexes with a 1-nucleotide gap, or a 2-nucleotide gap, were assessed. 84% of the input DNA substrate was ligated to the fully-paired acceptor in 10 sec, the earliest time analyzed (FIG. 6A). The size of the strand transfer product was 30 nucleotides, as expected (FIG. 7, lane 3). No 30-mer product was formed in the absence of the added acceptor strand (FIG. 7, lane 2).

Religation across a 1-nucleotide gap was highly efficient, albeit slow. 85% of the input substrate was joined across a 1-nucleotide gap to yield the expected 29-nucleotide product (FIG. 6A and FIG. 7, lane 4). The kinetic data in FIG. 6 fit well to a single exponential with an apparent rate constant of 0.005 sec$^{-1}$. Thus, single-turnover strand closure by topoisomerase across a 1-nucleotide gap was two orders of magnitude slower than the rate of joining across a fully paired nick. Vaccinia topoisomerase catalyzed strand transfer across a 2-nucleotide gap to form the anticipated 28-nucleotide product (FIG. 7, lane 5), but this reaction was feeble (FIG. 6A). Linear accumulation of the 2-nucleotide gap product was observed over a 2 h incubation, at which time only 10% of the input DNA had been joined. It was estimated based on the initial rate that religation across the 2-nucleotide gap was two orders of magnitude slower than joining across a 1-nucleotide gap (and hence four orders of magnitude slower than the rate of joining across a nick).

Similar experiments were performed using DNA acceptors that contained either 1 or 2 extra nucleotides at their 5' ends (FIG. 6C). Religation to these acceptors yielded labeled strand transfer products of 31 and 32 nucleotides, respectively (FIG. 7, lanes 6 and 7). 90% of the input DNA was religated to form the 1-nucleotide insertion product (FIG. 6C). A rate constant of 0.04 sec$^{-1}$ for religation with 1-nucleotide insertion was calculated. A similar endpoint was achieved in the formation of a 2-nucleotide insertion product, but the strand transfer rate was considerably slower (FIG. 6C). The observed rate constant for 2-nucleotide insertion was 0.0001 sec$^{-1}$, i.e., three orders of magnitude lower, than $k_{rel}$ at a nick.

Effect of 5' Acceptor Base Mismatch on Strand Transfer.

Figure 8:
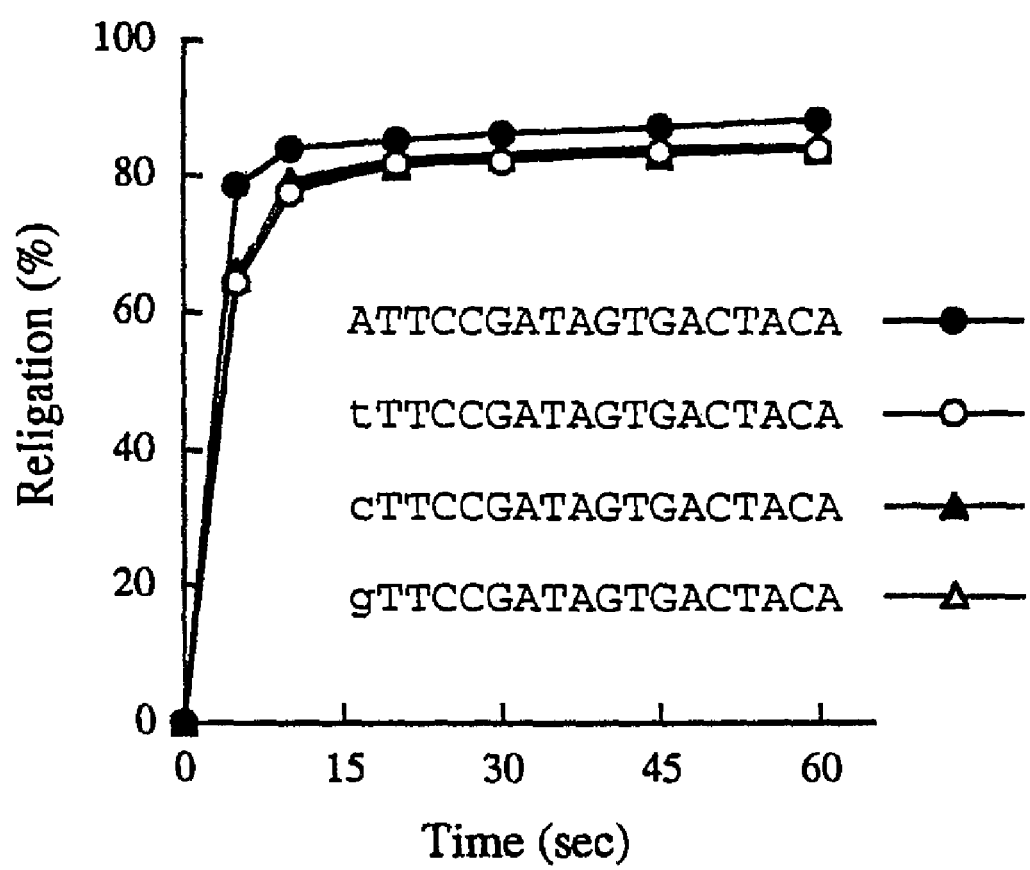
FIG. 8. (SEQ ID NOS: 4, 16-18) Strand transfer to DNA acceptors containing a single 5' base mismatch. Religation reactions were performed under single-turnover conditions as described under Materials and Methods. All DNA acceptors were included at a 50-fold molar excess over the input CCCTT-containing substrate. The structures of the fully complementary 18-mer and the three terminal-nucleotide variants are shown.

Strand transfer by topoisomerase to a set of 18-mer acceptors that were capable of base-pairing with the 5' tail of the donor complex from positions −2 to −18 (relative to the scissile +1 T:A base pair of the CCCTT element), but which have a base-mismatch at the −1 position immediately 3' of the scissile bond, was examined. The control acceptor, which has a normal −1 A:T base-pair, reacted to completion in 10 sec; 89% of the endpoint was achieved in 5 sec (FIG. 8). DNAs containing T:T, C:T, or G:T mispairs at the −1 position supported the same extent of strand transfer; 77% of the endpoint was attained in 5 sec in each case (FIG. 8). Thus, within the limits of detection of this experiment, mismatch at the −1 position had little effect on the strand transfer reaction. There are clear and instructive differences between the effects of base mismatches versus a single nucleotide deletion on the rate of the strand joining step.

Kinetics of Intramolecular Hairpin Formation.

Figure 9A:
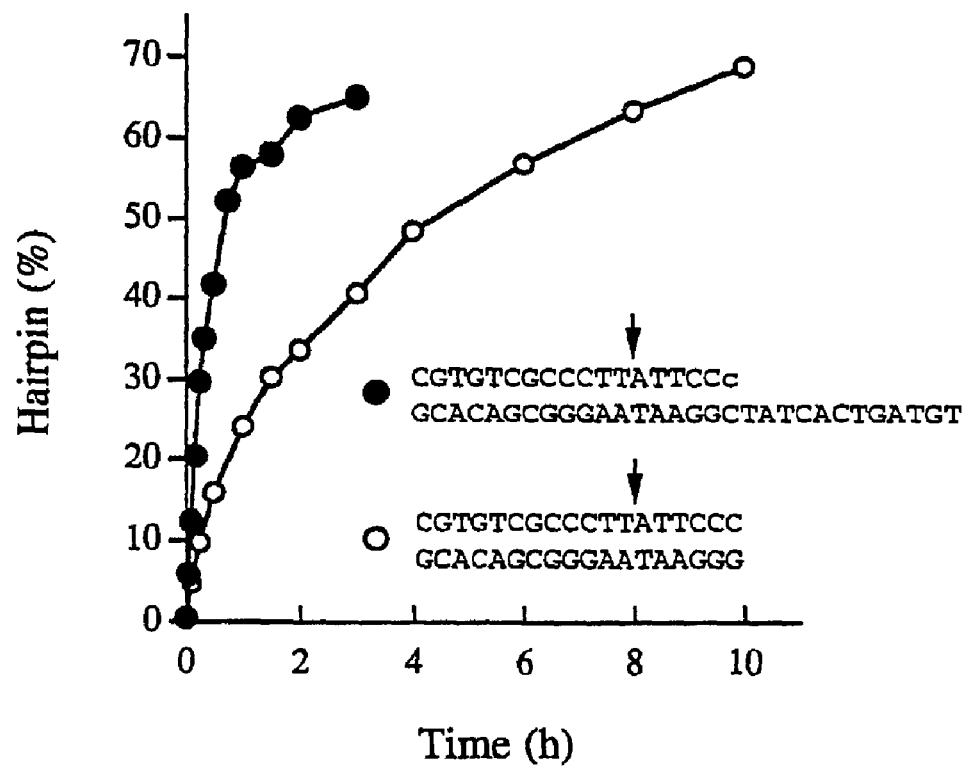
FIGS. 9A-B. Kinetics of intramolecular hairpin formation. (A) (SEQ ID NOS: 19-21) Hairpin formation without potential for base-pairing. DNA cleavage substrates were prepared by annealing the 5' $^{32}$P-labeled 18-mer scissile strand to a 30-mer complementary strand (filled circle) or an 18-mer complementary strand (circle); the structures of the substrates are shown with the topoisomerase cleavage sites indicated by arrows. Reaction mixtures containing (per 20 ul) 50 mM Tris HCl (pH 7.5), 0.5 pmol of DNA substrate, and 1 pmol of topoisomerase were incubated at 37° C. for 10 min. The mixtures were then adjusted to 0.3 M NaCl. Aliquots (20 ul) were withdrawn immediately prior to adding salt (time zero) and at various intervals after adding salt; the reactions were quenched immediately by adding an equal volume of stop solution (1% SDS, 95% formamide, 20 mM EDTA). The samples were heat-denatured and electrophoresed through a 17% polyacrylamide gel containing 7 M urea in TBE. The extent of intramolecular strand transfer (expressed as percent of the input labeled substrate converted to hairpin product) is plotted as a function of time after addition of NaCl. (B) (SEQ ID NOS: 19 and 22) Hairpin formation with potential for base-pairing. The structure of the 18-mer/30-mer cleavage substrate is shown, with the topoisomerase cleavage site indicated by an arrow. A reaction mixture containing (per 20 ut) 50 mM Tris HCl (pH 7.5), 0.5 pmol of DNA substrate, and 1 pmol of topoisomerase was incubated at 37° C. for 2 min. The mixtures were then adjusted to 0.3 M NaCl. Aliquots (20 ul) were withdrawn immediately prior to adding salt (time zero) and at various intervals after adding salt. The extent of intramolecular strand transfer is plotted as a function of time after addition of NaCl.

In the absence of an exogenous acceptor oligonucleotide, the 5'-OH terminus of the nonscissile strand of the 12-mer/30-mer covalent complex can flip back and act as the nucleophile in attacking the DNA-(3-phosphotyrosyl) bond (5). The reaction product is a hairpin molecule containing a 12-bp stem and an 18-nucleotide loop. The kinetics of this reaction were examined under single turnover conditions. In the experiment shown in FIG. 9A, 65% of the input CCCTT strand was converted to hairpin product in 3 h. The observed rate constant was 5.7×10$^{-4}$ sec$^{-1}$. In parallel, the rate of hairpin formation by the covalent complex formed on an 18-bp cleavage substrate (FIG. 9A) was analyzed. In this case, attack by the 5'-OH of the nonscissile strand yielded a hairpin molecule containing a 12-bp stem and a 6-nucleotide loop. 69% of the input CCCTT strand was converted to hairpin product in 10 h. The observed rate constant was 8.2×10$^{-5}$ sec$^{-1}$. Thus, the 18-nucleotide 5' tail was ~7 times more effective than the 6-mer 5' tail as the attacking nucleophile for strand transfer in cis. Note that hairpin formation by these covalent complexes occurs without any potential for base-pairing by the single-strand tails.

Figure 9B:
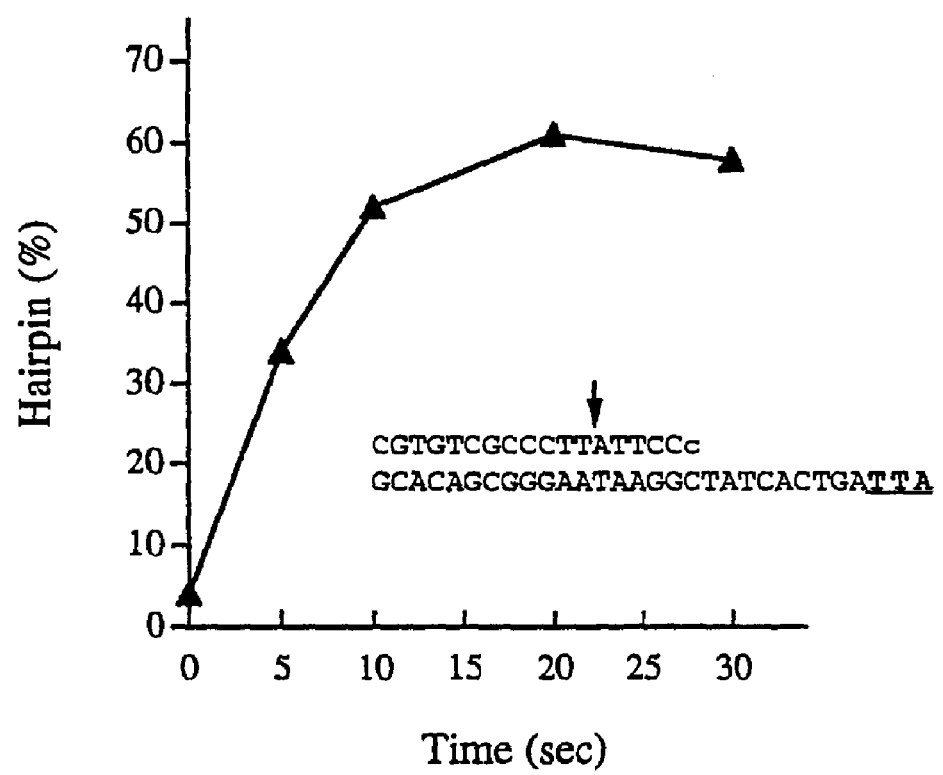

In order to examine the contribution of base-pairing to the rate of religation, the 5' terminal and penultimate bases of bottom strand of the 18-mer/30-mer substrate to 5'-AT (FIG. 9B) were altered. Now, the 5'-terminal three bases of the bottom strand (5'-ATT) are identical to the 5'-terminal bases of the leaving strand (5'-ATTCCC); hence, the single-strand tail is self-complementary and capable of forming three base-pairs adjacent to the scissile phosphate. Intramolecular hairpin formation on this DNA was extremely fast; the reaction was complete in 10-20 sec (FIG. 9B). The observed religation rate constant was 0.2 sec$^{-1}$. By comparing this value to the religation rate constant on the non-complementary 18-mer/30-mer substrate (FIG. 9A), it was surmised that 3 base-pairs accelerated the reaction ~350-fold.

Kinetics of Single-Turnover Cleavage of a CCCTT-Containing Hairpin Molecule

The 42-nucleotide 5' $^{32}$P-labeled hairpin product was gel-purified and tested as a substrate for covalent adduct formation by the vaccinia topoisomerase. 55% of the input radioactivity was transferred to the topoisomerase polypeptide in 15 sec at 37° C.; an endpoint of 90% transfer was attained in 60 sec (data not shown). The apparent rate constant for cleavage of the hairpin was 0.06 sec$^{-1}$. Thus, the topoisomerase rapidly and efficiently cleaved a CCCTT-containing molecule in which there were no standard paired bases downstream of the scissile phosphate. The hairpin cleavage rate constant is about one-fifth of $k_{cl}$ on the 18-mer/30-mer suicide substrate, which contains five paired bases of duplex DNA 3' of the CCCTT site.

Discussion

Vaccinia topoisomerase catalyzes a diverse repertoire of strand transfer reactions. Religation of the covalently bound DNA to a perfectly base-paired acceptor DNA oligonucleotide provides a model for the strand closure step of the DNA relaxation reaction. Here, the kinetics of strand transfer to alternative nucleic acid acceptors are analyzed. The findings provide new insights into the parameters that affect transesterification rate, illuminate the potential for topoisomerase to generate mutations in vivo, and suggest practical applications of vaccinia topoisomerase as an RNA modifying enzyme.

Sugar Specificity for Covalent Adduct Formation Resides within the CCCTT Element.

Vaccinia topoisomerase is apparently incapable of binding covalently to CCCUU-containing RNA strands. This is the case whether the CCCUU strand is part of an RNA-RNA or an RNA-DNA duplex (9). It has now been shown that the sugar specificity of the enzyme is attributable to a stringent requirement for DNA on the 5' side of the scissile phosphate, i.e., the CCCTT site must be DNA. Moreover, the CCCTT element must be a DNA-DNA duplex, because earlier experiments showed that a CCCTT strand is not cleaved when annealed to a complementary RNA strand (9). The RNA-DNA hybrid results are informative, because they suggest that the CCCTT site must adopt a B-form helical conformation in order to be cleaved. RNA and DNA polynucleotide chains adopt different conformations within an RNA-DNA hybrid, with the RNA strand retaining the A-form helical conformation (as found in dsRNA) while the DNA strand adopts a conformation that is neither strictly A nor B, but is instead intermediate in character between these two forms (20, 21). Vaccinia topoisomerase makes contacts with the nucleotide bases of the CCCTT site in the major groove (9, 22). It also makes contacts with specific phosphates of the CCCTT site (23). Adoption by the CCCTT site of a non-B conformation may weaken or preclude these contacts. The finding that vaccinia topoisomerase is relatively insensitive to the nucleotide sugar composition downstream of the scissile phosphate implies that the conformation of the helix in this portion of the ligand is not important for site recognition or reaction chemistry. Topoisomerase cleaves DNA-p-RNA strands in which the leaving strand is RNA. Indeed, the extent of cleavage at equilibrium is significantly higher than that achieved on a DNA-p-DNA strand.

Strand Transfer to RNA.

The increase in the cleavage-religation equilibrium constant $K_{eq}(=k_{cl}/k_{rel})$ on the DNA-p-RNA substrate can be explained by the finding that the rate of single-turnover RNA religation $k_{rel(RNA)}$ is about one-tenth of $k_{rel(DNA)}$. Nonetheless, the extent of religation to RNA is quite high, i.e., ~90% of the input CCCTT strand is religated to an 18-mer RNA acceptor strand in a 2 min reaction. It is shown that a CCCTT-containing DNA strand can be rapidly joined by topoisomerase to a transcript synthesized in vitro by bacteriophage RNA polymerase; ~30% of the RNA is transferred to the DNA strand in a 2-5 min reaction. This property can be exploited to 5' tag any RNA for which the 5' terminal RNA sequence is known, i.e., by designing a suicide DNA cleavage substrate for vaccinia topoisomerase in which the nonscissile strand is complementary to the 5' sequence of the intended RNA acceptor. Some practical applications include: (i) $^{32}$P-labeling of the 5' end of RNA and (ii) affinity labeling the 5' end of RNA, e.g., by using a biotinylated topoisomerase cleavage substrate. A potential avantage of topoisomerase-mediated RNA strand joining (compared with the standard T4 RNA ligase reaction) is that ligation by topoisomerase can be targeted by the investigator to RNAs of interest within a complex mixture of RNA molecules.

Frame-Shift and Missense Mutagenesis

It was reported earlier that vaccinia topoisomerase can religate to complementary DNA acceptors containing recessed ends or extra nucleotides, thereby generating the equivalent of frame-shift mutations (5). Similar reactions have been described by Henningfeld and Hecht (19) for the cellular type I topoisomerase. A key question is whether these aberrant religation reactions are robust enough to implicate topoisomerase as a potential mutagen in vivo. The kinetic analysis suggests that they are and provides the first clue as to what spectrum of frame-shift reactions are most likely to occur (taking into account only the intrinsic properties of the topoisomerase). For the vaccinia enzyme, the hierarchy of frame-shift generating religation reactions is as follows: +1 insertion >−1 deletion >+2 insertion >>−2 deletion.

The slowest of these topoisomerase catalyzed reactions is strand closure across a 2-nucleotide gap (initial rate=0.002% of input DNA religated/sec). In this situation, the attacking nucleophile is held in place at some distance from the DNA-protein phosphodiester by base-pairing to the nonscissile strand. Moving the 5' hydroxyl one base-pair closer to the phosphodiester enhances reaction rate by a factor of 100. Extra on-paired nucleotides appear to pose much less of an impediment to strand joining to form 1- or 2 nucleotide insertions. The active site of the topoisomerase may be able to accommodate extrahelical nucleotides; alternatively these nucleotides may intercalate into the DNA helix at the topoisomerase-induced nick.

There are two potential pathways for topoisomerase to form minus frame-shifts in vivo, which differ as to how the acceptor strand is generated: (i) the 5' end of the leaving strand can be trimmed by a nuclease, after which ligation could occur across the resulting gap; or (ii) a homologous DNA single strand attacks the covalent intermediate. The second pathway presumably requires a helicase in order to form the invading strand (and perhaps also to displace the leaving strand). In the case of plus frame-shifts, only the latter pathway would be available to the topoisomerase, i.e., because no mechanism exists to add nucleotides to the 5' terminus of the original leaving strand. No matter which pathway is taken, it is reasonable to assume that the most rapidly catalyzed mutagenic strand-joining reactions are the ones most likely to make their mark in vivo. If the religation reaction is slow, as for −2 frame-shifting, then the cell has greater opportunity to repair the mutagenic lesion, e.g., by removing the covalently bound topoisomerase. This could entail: (i) excision of a patch of the DNA strand to which the topoisomerase is bound; or (ii) hydrolysis of the topoisomerase-DNA adduct. An enzyme that catalyzes the latter reaction was discovered recently by Yang et al. (24).

Introducing a base mismatch at the −1 position immediately flanking the scissile phosphate has almost no effect on the rate of religation. This result is in stark contrast to the $10^{-2}$ rate effect of a 1-nucleotide gap. It is inferred that the −1 base mismatches do not significantly alter the proximity of the 5'-hydroxyl nucleophile of the terminal nucleotide to the scissile phosphate at enzyme's active site. The results indicate clearly that topoisomerase has the capacity to generate missense mutations in vitro. The single-strand invasion pathway involved above for frame-shift mutagenesis could, in principle, provide the opportunity for topoisomerase to create missense mutations in vivo. The kinetics of ligation in vitro suggest that topoisomerase-generated missense mutations would predominate over frame-shifts.

The Kinetic Contribution of Base Complementarity

Kinetic analysis of intramolecular hairpin formation by the vaccinia topoisomerase provides the first quantitative assessment of the role of base complementarity in strand closure. The rate constant for attack on the DNA-(3'-phosphotyrosyl) bond by a non-pairing 18-nucleotide single strand linked in cis to the covalent complex was $5.7 \times 10^{-4}$ $sec^{-1}$. Altering only the terminal bases of the single-strand tail to allow base-pairing at the −1, −2, and −3 positions increased the rate constant for hairpin formation by 350-fold. The rate of religation in cis with 3 potential base-pairs was nearly the same as the rate of religation to a non-covalently linked acceptor strand that forms 18 base pairs 3' of the scissile bond. The ability of the covalently bound enzyme to take up and rapidly rejoin DNA strands with only three complementary nucleotides lends credence to the suggestion that vaccinia topoisomerase catalyzes the formation of recombination intermediates in vivo (25), either via strand invasion or by reciprocal strand transfer between two topoisomerase-DNA complexes.

Generation of Gene Sequences

The use of a DNA-tagged RNA to clone gene sequences was evaluated using 96 base test RNA fragment of known sequence (GGG AGA CCC AAG CTC GCC CGG TTC TTT TTG TCA AGA CCG ACC TGT CCG GTG CCC TGA ATG AAC TGC AGG ACG AGG CAG CGC GGC TAT CGT GGC TGG) (SEQ ID NO: 39). This test RNA was synthesized using a T7 Invitrotranscription kit from Ambion Co. using protocols supplied by the manufacturer.

A topoisomerase-DNA intermediate was generated as follows: 25 ul of streptavidin conjugated Dynabeads (Dynal) were washed twice with 25 l of 2× B&W buffer (10 mM Tris pH 7.5, 1 mM EDTA, 2 M NaCl) in an eppendorf tube then resuspended in 50 ul 1× B&W buffer. 1.5 ug of a biotinylated oligo (TOPOB1) and. 75 ug of two annealing oligos (TOPOP2, TOPOP3) were added to the beads and heated to 70° C. for 5 minutes, then cooled on ice for 2 minutes. The beads were then washed twice with 25 pi each of NEB #1 buffer (New England Biolabs-10 mM Bis Tris Propane-HCl, 10 mM MgCl2, 1 mMDTT pH7.0 @ 25° to remove any unannealed oligonucleotides. The oligonucleotides were synthesized by Dalton Biochemicals (Canada) and had the following sequences:

```
                                          (SEQ ID NO: 40)
TOPOB1-
5'B-GTTTTGGCTCCCATATACGACTCGCCCTTNTTCCGATAGTG

TOPOP2-5'-NAAGGGCGAGTC             (SEQ ID NO: 41)

TOPOP3-5'-CACTATCGGAA.              (SEQ ID NO: 42)
```

The 5' end of TOPOB1 was biotinylated by using a biotinylated guanine nucleotide during that round of automated synthesis.

After the annealing step, the DNA substrate was modified using vaccinia topoisomerase basically as previously described. Approximately 2.5 g of vaccinia Topoisomerase 1 was added to the beads in 25 μl of 1×NEB #1 buffer. This mixture was placed on a rotating wheel for 5 minutes at room temperature then washed three times with 25 μl of 1×NEB #1 buffer. Approximately 100-200 ng of the 96mer RNA was added to the washed topoisomerase-DNA intermediate bound beads in 10 μl, then 15 μl of 0.5 M NaCl (final conc. 0.3 M) was added, and the tube was rotated for 5 minutes at room temperature.

The DNA-tagged RNA bound beads were next washed twice with 1× RT buffer (cDNA Cycle Kit, Invitrogen, Carlsbad, Calif., cat. # L1310-01), primed with RT96 (synthesis of first strand) and PCR performed using the cDNA Cycle Kit according to the manufacturer's instructions and primers PCR96 and PCR53.

```
RT96-5'-CCACGATAGCCGCGCT          (SEQ ID NO: 43)

PCR96-CGTCCTGCAGTTCATTCAG         (SEQ ID NO: 44)

PCR53-GGCTCCCATATACGACTC.         (SEQ ID NO: 45)
```

The reaction cycles were as follows: 2 minutes at 94° C., then 25-35 cycles (10 sec/cycle) 94° C., 55° C. and 72° C., followed by 5 minutes at 72° C. The resulting amplified cDNA was inserted into a plasmid vector using a TOPO™TA cloning Kit (Invitrogen, Carlsbad, Calif., cat. #K4500-01) used according to the manufacturer's instructions.

While the foregoing has been presented with reference to particular embodiments of the invention, it will be appreciated by those skilled in the art that changes in these embodiments may be made without departing from the principles and spirit of the invention, the scope of which is defined by the appended claims.

REFERENCES

1. Shuman, S., and Prescott, J. (1990) J. Biol. Chem. 265, 17826-17836
2. Shuman, S. (1991) J. Biol. Chem. 266, 1796-1803.
3. Shuman, S. (1991) J. Biol. Chem. 266, 11372-11279.
4. Shuman, S., Kane, E. M., and Morham, S. G. (1989) Proc. Natl. Acad. Sci. USA. 86, 9793-9797.
5. Shuman, S. (1992) J. Biol. Chem. 267, 8620-8627.
6. Shuman, S. (1992) J. Biol. Chem. 267, 16755-16758.
7. Sekiguchi, J., Seeman, N. C., and Shuman, S. (1996) Proc. Natl. Acad. Sci. USA 93, 785-789.
8. Stivers, J. T., Shuman, S., and Mildvan, A. S. (1994) Biochemistry 33, 327-339.
9. Shuman, S., and Turner, J. (1993) J. Biol. Chem. 268, 18943-18950.
10. Petersen, B. O., Wittschieben, J., and Shuman, S. (1996) J. Mol. Biol. 263, 181-195.
11. Petersen, B. O., and Shuman, S. (1997) J. Biol. Chem. 272, 3891-3896.
12. Petersen, B. O., and Shuman, s. (1997) Nucleic Acids Res. (in press).
13. Shuman, S. (1994) J. Biol. Chem. 269, 32678-32684.
14. Shuman, S. (1995) Biochemistry 34, 16138-16147.
15. Sekiguchi, J., and Shuman, s. (1997) Nucleic Acids Res. 25, 727-734.
16. Shuman, S., Golder, M., and Moss, B. (1988) J. Biol. Chem. 263, 16401-16407.
17. Morham, S. G., and Shuman, S. (1992) J. Biol. Chem. 267, 15984-15992.
18. Cheng, C., Wang, L. K., Sekiguchi, J., and Shuman, S. (1997) J. Biol. Chem. 272, 8263-8269.
19. Henningfeld, K. A., and Hecht, S. M. (1995) Biochemistry 34, 6120-6129.
20. Salazar, M., Federoff, O. Y., Miller, J. M., Ribeiro, N. S., and Reid, B. R. (1993) Biochemistry 32, 4207-4215.
21. Arnott, S., Chandrasekara, R., Millane, R. P., and Park, H. (1986) J. Mol. Biol. 188, 631-640.
22. Sekiguchi, J., and Shuman, S. (1996) EMBO J. 15, 3448-3457.
23. Sekiguchi, J., and Shuman, S. (1994) J. Biol. Chem. 269, 31731-31734.
24. Yang, S. W., Burgin, A. B., Huizenga, B. N., Robertson, C. A., Yao, K. C., and Nash, H. A. Natl. Acad. Sci. USA 93, 11534-11539.
25. Shuman, S. (1991) Proc. Natl. Acad. Sci. USA 88, 10104-10108.

What is claimed is:

1. A method of covalently joining a DNA strand to an RNA strand comprising:
   (a) forming a vaccinia topoisomerase-DNA intermediate by incubating a DNA cleavage substrate comprising a vaccinia topoisomerase cleavage site with a vaccinia topoisomerase specific for that site, wherein the vaccinia topoisomerase-DNA intermediate has one or more 5' single-strand tails; and
   (b) adding to the vaccinia topoisomerase-DNA intermediate an acceptor RNA strand complementary to the 5' single-strand tail under conditions permitting a ligation of the covalently bound DNA strand of the vaccinia topoisomerase-DNA intermediate to the RNA acceptor strand and dissociation of the vaccinia topoisomerase, thereby covalently joining the DNA strand to the RNA strand.

2. A method of claim 1, wherein the DNA cleavage substrate is created by hybridizing a DNA strand having a vaccinia topoisomerase cleavage site to a complementary DNA strand, thereby forming a DNA cleavage substrate having a vaccinia topoisomerase cleavage site and a oligonucleotide leaving group located 3' of a scissile bond.

3. A method of claim 1, wherein the DNA cleavage substrate is a plasmid vector comprising a vaccinia topoisomerase cleavage site.

4. The method of claim 1, wherein the vaccinia topoisomerase cleavage site is a sequence comprising CCCTT.

5. The method of claim 1, wherein the DNA strand comprising a vaccinia topoisomerase cleavage site is radiolabelled.

6. The method of claim 5, wherein the radiolabel is $^{32}P$ or a radiohalogen.

7. The method of claim 1, wherein the DNA strand having a vaccinia topoisomerase cleavage site is labeled with a biotin moiety.

8. The method of claim 1, wherein the vaccinia topoisomerase-bound DNA intermediate and the acceptor RNA strand are ligated in vitro.

9. A method of tagging a 5' end of an RNA molecule comprising:
   (a) forming a vaccinia topoisomerase-DNA intermediate by incubating a DNA cleavage substrate comprising a vaccinia topoisomerase cleavage site with a vaccinia topoisomerase specific for that site, wherein the vaccinia topoisomerase-DNA intermediate has one or more 5' single-strand tails; and
   (b) adding to the vaccinia topoisomerase-DNA intermediate a 5'-hydroxyl terminated RNA molecule complementary to the 5' single-strand tail under conditions permitting ligation of the covalently bound DNA strand of the vaccinia topoisomerase-DNA intermediate to the RNA molecule and dissociation of the vaccinia topoisomerase, thereby forming a 5' end tagged DNA-RNA ligation product.

10. A method of claim 9, wherein the 5'-hydroxyl terminated RNA molecule is the product of in vitro synthesis or isolation from cells or tissues.

11. The method of claim 10, wherein the RNA molecule is dephosphorylated after synthesis or isolation.

12. The method of claim 11, wherein the dephosphorylation is achieved by treatment of the RNA molecule with alkaline phosphatase.

13. A method of claim 9, wherein the DNA cleavage substrate is created by hybridizing a DNA strand having a vaccinia topoisomerase cleavage site to a complementary DNA strand, thereby forming a DNA cleavage substrate having a vaccinia topoisomerase cleavage site and a oligonucleotide leaving group located 3' of a scissile bond.

14. The method of claim 9, wherein the cleavage site comprises CCCTT.

15. The method of claim 9, wherein the vaccinia topoisomerase-DNA intermediate comprises a 5' end label.

16. The method of claim 15, wherein the 5' end label is a biotin moiety, a chitin binding domain, or a glutathione-S-transferase moiety.

17. The method of claim 15, further comprising immobilizing the 5' end labeled vaccinia topoisomerase-DNA intermediate on a solid support prior to the addition of the 5'-hydroxyl terminated RNA molecule.

18. The method of claim 17, wherein the solid support comprises streptavidin, avidin, chitin or glutathione.

19. The method of claim 17, further comprising, purifying a biotinylated 5' end tagged DNA-RNA ligation product by separating the solid support to which the end labeled DNA-RNA ligation product is immobilized from a liquid phase comprising unmodified RNA.

* * * * *

SEQUENCE LISTING

```
<160> NUMBER OF SEQ ID NOS: 48

<210> SEQ ID NO 1
<211> LENGTH: 5
<212> TYPE: DNA
<213> ORGANISM: Artificial Sequence
<220> FEATURE:
<223> OTHER INFORMATION: Synthetic topoisomerase binding sequence

<400> SEQUENCE: 1 ccctt                                                                  5

<210> SEQ ID NO 2
<211> LENGTH: 5
<212> TYPE: DNA
<213> ORGANISM: Artificial Sequence
<220> FEATURE:
<223> OTHER INFORMATION: Synthetic topoisomerase binding sequence
<220> FEATURE:
<221> NAME/KEY: misc_feature
```

```
<222> LOCATION: (1)..(1)
<223> OTHER INFORMATION: n=T or C

<400> SEQUENCE: 2 ncctt                                                                      5

<210> SEQ ID NO 3
<211> LENGTH: 18
<212> TYPE: DNA
<213> ORGANISM: Artificial Sequence
<220> FEATURE:
<223> OTHER INFORMATION: Synthetic proximal 18-mer DNA strand

<400> SEQUENCE: 3
catatccgtg tcgcccctt                                                      18

<210> SEQ ID NO 4
<211> LENGTH: 18
<212> TYPE: DNA
<213> ORGANISM: Artificial Sequence
<220> FEATURE:
<223> OTHER INFORMATION: Synthetic distal 18-mer DNA strand

<400> SEQUENCE: 4
attccgatag tgactaca                                                       18

<210> SEQ ID NO 5
<211> LENGTH: 36
<212> TYPE: DNA
<213> ORGANISM: Artificial Sequence
<220> FEATURE:
<223> OTHER INFORMATION: Synthetic 36-mer DNA strand

<400> SEQUENCE: 5
tgtagtcact atcggaataa gggcgacacg gatatg                                   36

<210> SEQ ID NO 6
<211> LENGTH: 12
<212> TYPE: DNA
<213> ORGANISM: Artificial Sequence
<220> FEATURE:
<223> OTHER INFORMATION: Synthetic topo-DNA complex sequence

<400> SEQUENCE: 6
cgtgtcgccc tt                                                             12

<210> SEQ ID NO 7
<211> LENGTH: 30
<212> TYPE: DNA
<213> ORGANISM: Artificial Sequence
<220> FEATURE:
<223> OTHER INFORMATION: Synthetic topo-DNA complex sequence

<400> SEQUENCE: 7
tgtagtcact atcggaataa gggcgacacg                                          30

<210> SEQ ID NO 8
<211> LENGTH: 18
<212> TYPE: DNA
<213> ORGANISM: Artificial Sequence
<220> FEATURE:
<223> OTHER INFORMATION: Synthetic 18-mer acceptor strand DNA

<400> SEQUENCE: 8
attccgatag tgactaca                                                       18
```

```
<210> SEQ ID NO 9
<211> LENGTH: 18
<212> TYPE: RNA
<213> ORGANISM: Artificial Sequence
<220> FEATURE:
<223> OTHER INFORMATION: Synthetic 18-mer acceptor strand RNA

<400> SEQUENCE: 9
auuccgauag ugacuaca                                                 18

<210> SEQ ID NO 10
<211> LENGTH: 30
<212> TYPE: DNA
<213> ORGANISM: Artificial Sequence
<220> FEATURE:
<223> OTHER INFORMATION: Synthetic topo-DNA complex sequence

<400> SEQUENCE: 10
gctccagctt ttgttcccaa gggcgacacg                                    30

<210> SEQ ID NO 11
<211> LENGTH: 36
<212> TYPE: RNA
<213> ORGANISM: Artificial Sequence
<220> FEATURE:
<223> OTHER INFORMATION: Synthetic RNA acceptor sequence
<220> FEATURE:
<221> NAME/KEY: misc_feature
<222> LOCATION: (19)..(36)
<223> OTHER INFORMATION: n=A, U, C, or G

<400> SEQUENCE: 11
gggaacaaaa gcuggagcnn nnnnnnnnnn nnnnnn                             36

<210> SEQ ID NO 12
<211> LENGTH: 17
<212> TYPE: DNA
<213> ORGANISM: Artificial Sequence
<220> FEATURE:
<223> OTHER INFORMATION: Synthetic 17-mer oligonucleotide gap

<400> SEQUENCE: 12
ttccgatagt gactaca                                                  17

<210> SEQ ID NO 13
<211> LENGTH: 16
<212> TYPE: DNA
<213> ORGANISM: Artificial Sequence
<220> FEATURE:
<223> OTHER INFORMATION: Synthetic 16-mer DNA strand

<400> SEQUENCE: 13
tccgatagtg actaca                                                   16

<210> SEQ ID NO 14
<211> LENGTH: 19
<212> TYPE: DNA
<213> ORGANISM: Artificial Sequence
<220> FEATURE:
<223> OTHER INFORMATION: Synthetic 19-mer oligonucleotide

<400> SEQUENCE: 14
aattccgata gtgactaca                                                19

<210> SEQ ID NO 15
<211> LENGTH: 20
<212> TYPE: DNA
<213> ORGANISM: Artificial Sequence
```

```
<220> FEATURE:
<223> OTHER INFORMATION: Synthetic 20-mer acceptor

<400> SEQUENCE: 15
aaattccgat agtgactaca                                                    20

<210> SEQ ID NO 16
<211> LENGTH: 18
<212> TYPE: DNA
<213> ORGANISM: Artificial Sequence
<220> FEATURE:
<223> OTHER INFORMATION: Synthetic terminal nucleotide variant 1

<400> SEQUENCE: 16
tttccgatag tgactaca                                                      18

<210> SEQ ID NO 17
<211> LENGTH: 18
<212> TYPE: DNA
<213> ORGANISM: Artificial Sequence
<220> FEATURE:
<223> OTHER INFORMATION: Synthetic terminal nucleotide variant 2

<400> SEQUENCE: 17
cttccgatag tgactaca                                                      18

<210> SEQ ID NO 18
<211> LENGTH: 18
<212> TYPE: DNA
<213> ORGANISM: Artificial Sequence
<220> FEATURE:
<223> OTHER INFORMATION: Synthetic terminal nucleotide variant 3

<400> SEQUENCE: 18
gttccgatag tgactaca                                                      18

<210> SEQ ID NO 19
<211> LENGTH: 18
<212> TYPE: DNA
<213> ORGANISM: Artificial Sequence
<220> FEATURE:
<223> OTHER INFORMATION: Synthetic 18-mer scissile strand

<400> SEQUENCE: 19
cgtgtcgccc ttattccc                                                      18

<210> SEQ ID NO 20
<211> LENGTH: 30
<212> TYPE: DNA
<213> ORGANISM: Artificial Sequence
<220> FEATURE:
<223> OTHER INFORMATION: Synthetic 30-mer complementary strand

<400> SEQUENCE: 20
tgtagtcact atcggaataa gggcgacacg                                         30

<210> SEQ ID NO 21
<211> LENGTH: 18
<212> TYPE: DNA
<213> ORGANISM: Artificial Sequence
<220> FEATURE:
<223> OTHER INFORMATION: Synthetic 18-mer complementary strand

<400> SEQUENCE: 21
gggaataagg gcgacacg                                                      18
```

```
<210> SEQ ID NO 22
<211> LENGTH: 30
<212> TYPE: DNA
<213> ORGANISM: Artificial Sequence
<220> FEATURE:
<223> OTHER INFORMATION: Synthetic 30-mer complementary strand

<400> SEQUENCE: 22
attagtcact atcggaataa gggcgacacg                                    30

<210> SEQ ID NO 23
<211> LENGTH: 25
<212> TYPE: DNA
<213> ORGANISM: Artificial Sequence
<220> FEATURE:
<223> OTHER INFORMATION: Synthetic biotinylated DNA substrate sequence

<400> SEQUENCE: 23
aacatatccg tgtcgccctt gggcg                                         25

<210> SEQ ID NO 24
<211> LENGTH: 24
<212> TYPE: DNA
<213> ORGANISM: Artificial Sequence
<220> FEATURE:
<223> OTHER INFORMATION: Synthetic biotinylated DNA substrate sequence

<400> SEQUENCE: 24
cccaattcgc ccaagggcga cacg                                          24

<210> SEQ ID NO 25
<211> LENGTH: 20
<212> TYPE: DNA
<213> ORGANISM: Artificial Sequence
<220> FEATURE:
<223> OTHER INFORMATION: Synthetic enzyme-DNA donor duplex complex
      sequence

<400> SEQUENCE: 25
aacatatccg tgtcgccctt                                               20

<210> SEQ ID NO 26
<211> LENGTH: 30
<212> TYPE: RNA
<213> ORGANISM: Artificial Sequence
<220> FEATURE:
<223> OTHER INFORMATION: Synthetic 5' single-strand tail of donor duplex

<400> SEQUENCE: 26
gggcgaauug gguaccgggc cccccucga                                     30

<210> SEQ ID NO 27
<211> LENGTH: 50
<212> TYPE: DNA
<213> ORGANISM: Artificial Sequence
<220> FEATURE:
<223> OTHER INFORMATION: Synthetic 50-mer religation product

<400> SEQUENCE: 27
aacatatccg tgtcgccctt gggcgaauug gguaccgggc cccccucga               50

<210> SEQ ID NO 28
<211> LENGTH: 40
<212> TYPE: DNA
<213> ORGANISM: Artificial Sequence
<220> FEATURE:
<223> OTHER INFORMATION: Synthetic DNA tag sequence
<220> FEATURE:
```

```
<221> NAME/KEY: misc_feature
<222> LOCATION: (29)..(29)
<223> OTHER INFORMATION: n=A, T, C or G

<400> SEQUENCE: 28
gtttggctcc catatacgac tcgcccttnt tccgatagtg                           40

<210> SEQ ID NO 29
<211> LENGTH: 24
<212> TYPE: DNA
<213> ORGANISM: Artificial Sequence
<220> FEATURE:
<223> OTHER INFORMATION: Synthetic DNA tag sequence
<220> FEATURE:
<221> NAME/KEY: misc_feature
<222> LOCATION: (12)..(12)
<223> OTHER INFORMATION: n=A, T, C, or G

<400> SEQUENCE: 29
cactatcgga anaagggcga gtcg                                            24

<210> SEQ ID NO 30
<211> LENGTH: 28
<212> TYPE: DNA
<213> ORGANISM: Artificial Sequence
<220> FEATURE:
<223> OTHER INFORMATION: Synthetic DNA tag sequence

<400> SEQUENCE: 30
gtttggctcc catatacgac tcgcccctt                                       28

<210> SEQ ID NO 31
<211> LENGTH: 13
<212> TYPE: DNA
<213> ORGANISM: Artificial Sequence
<220> FEATURE:
<223> OTHER INFORMATION: Synthetic DNA tag sequence
<220> FEATURE:
<221> NAME/KEY: misc_feature
<222> LOCATION: (1)..(1)
<223> OTHER INFORMATION: n=A, T, C, or G

<400> SEQUENCE: 31
naagggcgag tcg                                                        13

<210> SEQ ID NO 32
<211> LENGTH: 16
<212> TYPE: RNA
<213> ORGANISM: Artificial Sequence
<220> FEATURE:
<223> OTHER INFORMATION: Synthetic 16-mer proximal RNA strand sequence

<400> SEQUENCE: 32
cauauccgug ucccuu                                                     16

<210> SEQ ID NO 33
<211> LENGTH: 18
<212> TYPE: RNA
<213> ORGANISM: Artificial Sequence
<220> FEATURE:
<223> OTHER INFORMATION: Synthetic 18-mer distal RNA strand sequence

<400> SEQUENCE: 33
auuccgauag ugacuaca                                                   18

<210> SEQ ID NO 34
<211> LENGTH: 5
<212> TYPE: RNA
```

```
<213> ORGANISM: Artificial Sequence
<220> FEATURE:
<223> OTHER INFORMATION: Synthetic topoisomerase non-binding sequence

<400> SEQUENCE: 34 cccuu                                                                     5

<210> SEQ ID NO 35
<211> LENGTH: 5
<212> TYPE: DNA
<213> ORGANISM: Artificial Sequence
<220> FEATURE:
<223> OTHER INFORMATION: Synthetic 5-nucleotide leaving group

<400> SEQUENCE: 35 attcc                                                                     5

<210> SEQ ID NO 36
<211> LENGTH: 30
<212> TYPE: DNA
<213> ORGANISM: Artificial Sequence
<220> FEATURE:
<223> OTHER INFORMATION: Synthetic 30-mer DNA-RNA strand

<400> SEQUENCE: 36
cgtgtcgccc ttauuccgau agugacuaca                                          30

<210> SEQ ID NO 37
<211> LENGTH: 13
<212> TYPE: DNA
<213> ORGANISM: Artificial Sequence
<220> FEATURE:
<223> OTHER INFORMATION: Synthetic alkaline hydrolysis product sequence

<400> SEQUENCE: 37
cgtgtcgccc tta                                                            13

<210> SEQ ID NO 38
<211> LENGTH: 6
<212> TYPE: DNA
<213> ORGANISM: Artificial Sequence
<220> FEATURE:
<223> OTHER INFORMATION: Synthetic 6-nucleotide leaving strand sequence

<400> SEQUENCE: 38 attccc                                                                    6

<210> SEQ ID NO 39
<211> LENGTH: 96
<212> TYPE: DNA
<213> ORGANISM: Artificial Sequence
<220> FEATURE:
<223> OTHER INFORMATION: Synthetic 96 base DNA-tagged RNA sequence

<400> SEQUENCE: 39
gggagaccca agctcgcccg gttcttttg tcaagaccga cctgtccggt gccctgaatg          60
aactgcagga cgaggcagcg cggctatcgt ggctgg                                   96

<210> SEQ ID NO 40
<211> LENGTH: 41
<212> TYPE: DNA
<213> ORGANISM: Artificial Sequence
<220> FEATURE:
<223> OTHER INFORMATION: Synthetic unannealed oligonucleotide sequence 1
<220> FEATURE:
<221> NAME/KEY: misc_feature
<222> LOCATION: (30)..(30)
```

<223> OTHER INFORMATION: n= A, T, C, or G

<400> SEQUENCE: 40
gttttggctc ccatatacga ctcgcccttn ttccgatagt g                          41

<210> SEQ ID NO 41
<211> LENGTH: 12
<212> TYPE: DNA
<213> ORGANISM: Artificial Sequence
<220> FEATURE:
<223> OTHER INFORMATION: Synthetic unannealed oligonucleotide sequence 2
<220> FEATURE:
<221> NAME/KEY: misc_feature
<222> LOCATION: (1)..(1)
<223> OTHER INFORMATION: n= A, T, C, or G

<400> SEQUENCE: 41
naagggcgag tc                                                          12

<210> SEQ ID NO 42
<211> LENGTH: 11
<212> TYPE: DNA
<213> ORGANISM: Artificial Sequence
<220> FEATURE:
<223> OTHER INFORMATION: Synthetic unannealed oligonucleotide sequence 3

<400> SEQUENCE: 42
cactatcgga a                                                           11

<210> SEQ ID NO 43
<211> LENGTH: 16
<212> TYPE: DNA
<213> ORGANISM: Artificial Sequence
<220> FEATURE:
<223> OTHER INFORMATION: Synthetic amplified cDNA sequence 1

<400> SEQUENCE: 43
ccacgatagc cgcgct                                                      16

<210> SEQ ID NO 44
<211> LENGTH: 19
<212> TYPE: DNA
<213> ORGANISM: Artificial Sequence
<220> FEATURE:
<223> OTHER INFORMATION: Synthetic amplified cDNA sequence 1

<400> SEQUENCE: 44
cgtcctgcag ttcattcag                                                   19

<210> SEQ ID NO 45
<211> LENGTH: 18
<212> TYPE: DNA
<213> ORGANISM: Artificial Sequence
<220> FEATURE:
<223> OTHER INFORMATION: Synthetic amplified cDNA sequence 3

<400> SEQUENCE: 45
ggctcccata tacgactc                                                    18

<210> SEQ ID NO 46
<211> LENGTH: 5
<212> TYPE: PRT
<213> ORGANISM: Artificial Sequence
<220> FEATURE:
<223> OTHER INFORMATION: Synthetic

<400> SEQUENCE: 46

```
Phe His His Thr Thr
1               5

<210> SEQ ID NO 47
<211> LENGTH: 16
<212> TYPE: RNA
<213> ORGANISM: Artificial Sequence
<220> FEATURE:
<223> OTHER INFORMATION: Synthetic

<400> SEQUENCE: 47
cauauccgug ucccuu                                                        16

<210> SEQ ID NO 48
<211> LENGTH: 18
<212> TYPE: RNA
<213> ORGANISM: Artificial Sequence
<220> FEATURE:
<223> OTHER INFORMATION: Synthetic

<400> SEQUENCE: 48
auuccgauag ugacuaca                                                      18
```